(12) United States Patent
Kaufmann et al.

(10) Patent No.: US 8,729,048 B2
(45) Date of Patent: May 20, 2014

(54) METHODS AND MATERIALS FOR ASSESSING RESPONSIVENESS TO PARP INHIBITORS AND PLATINATING AGENTS

(71) Applicant: Mayo Foundation for Medical Education and Research, Rochester, MN (US)

(72) Inventors: Scott H. Kaufmann, Rochester, MN (US); Anand G. Patel, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 6 days.

(21) Appl. No.: 13/679,756

(22) Filed: Nov. 16, 2012

(65) Prior Publication Data
US 2013/0224312 A1   Aug. 29, 2013

Related U.S. Application Data

(60) Provisional application No. 61/562,735, filed on Nov. 22, 2011.

(51) Int. Cl.
| *A61K 31/70* | (2006.01) |
| *A61K 31/55* | (2006.01) |
| *A61K 31/495* | (2006.01) |
| *A61K 31/44* | (2006.01) |
| *A61K 31/415* | (2006.01) |
| *A61K 31/335* | (2006.01) |
| *A61K 31/28* | (2006.01) |
| *A61K 31/165* | (2006.01) |
| *A61K 33/24* | (2006.01) |

(52) U.S. Cl.
USPC ........ 514/49; 514/212.06; 514/248; 514/283; 514/394; 514/449; 514/492; 514/619; 424/649

(58) Field of Classification Search
USPC .............. 514/49, 212.06, 248, 283, 394, 449, 514/492, 619; 424/649
See application file for complete search history.

(56) References Cited

U.S. PATENT DOCUMENTS

| 2009/0017010 A1 | 1/2009 | Lieber et al. |
| 2009/0062196 A1 | 3/2009 | D'Andrea et al. |

OTHER PUBLICATIONS

Brem and Hall, "XRCC1 is required for DNA single-strand break repair in human cells," *Nucleic Acids Res.*, 33(8):2512-2520, May 2005.
Bryant et al., "Specific killing of BRCA2-deficient tumours with inhibitors of poly(ADP-ribose) polymerase," *Nature*, 434(7035):913-917, Apr. 2005.
Caldecott, "XRCC1 and DNA strand break repair," *DNA Repair Amst*, 2(9):955-969, Sep. 2003.

Chan et al., "Autophosphorylation of the DNA-dependent protein kinase catalytic subunit is required for rejoining of DNA double-strand breaks," *Genes Dev.*, 16(18):2333-2338, Sep. 2002.
Drouet et al., "Interplay between Ku, Artemis, and the DNA-dependent protein kinase catalytic subunit at DNA ends," *J. Biol. Chem.*, 281(31):27784-27793, Sep. 2006.
Farmer et al., "Targeting the DNA repair defect in BRCA mutant cells as a therapeutic strategy," *Nature*, 434(7035):917-921, Apr. 2005.
Fattah et al., "Ku regulates the non-homologous end joining pathway choice of DNA double-strand break repair in human somatic cells," *PLoS Genet.*, 6(2):e1000855, Feb. 2010.
GenBank® GI No. 10863945 GenBank® Accession No. NP_066964, "X-ray repair cross-complementing protein 5 [*Homo sapiens*]," Nov. 12, 2010, 3 pages.
GenBank® GI No. 110224474 GenBank® Accession No. NM_000314, "*Homo sapiens* phosphatase and tensin homolog (PTEN), mRNA," Nov. 14, 2010, 5 pages.
GenBank® GI No. 119395733 GenBank® Accession No. NM_000059, "*Homo sapiens* breast cancer 2, early onset (BRCA2), mRNA," Nov. 15, 2010, 9 pages.
GenBank® GI No. 119395734 GenBank® Accession No. NP_000050, "breast cancer type 2 susceptibility protein [*Homo sapiens*]," Nov. 15, 2010, 3 pages.
GenBank® GI No. 126032349 GenBank® Accession No. NM_001081640, "*Homo sapiens* protein kinase, DNA-activated, catalytic polypeptide (PRKDC), transcript variant 2, mRNA," Oct. 10, 2010, 12 pages.
GenBank® GI No. 126032350 GenBank® Accession No. NP_001075109, "DNA-dependent protein kinase catalytic subunit isoform 2 [*Homo sapiens*]," Oct. 10, 2010, 3 pages.
GenBank® GI No. 13376142 GenBank® Accession No. NP_079058.1, "non-homologous end joining factor 1 [*Homo sapiens*]," Nov. 4, 2010, 3 pages.
GenBank® GI No. 148539893 GenBank® Accession No. NM_001098268, "*Homo sapiens* ligase IV, DNA, ATP-dependent (LIG4), transcript variant 3, mRNA," Nov. 4, 2010, 4 pages.
GenBank® GI No. 148539894 GenBank® Accession No. NP_001091738, "DNA ligase 4 [*Homo sapiens*]," Nov. 4, 2010, 3 pages.
GenBank® GI No. 187607429 GenBank® Accession No. NM_024782, "*Homo sapiens* nonhomologous end joining factor 1 (NHEJ1), mRNA," Nov. 4, 2010, 4 pages.
GenBank® GI No. 195963391 GenBank® Accession No. NM_021141, "*Homo sapiens* X-ray repair complementing defective repair in Chinese hamster cells 5 (double-strand-break rejoining) (XRCC5), mRNA," Nov. 12, 2010, 6 pages.
GenBank® GI No. 196162694 GenBank® Accession No. NM_003401, "*Homo sapiens* X-ray repair complementing defective repair in Chinese hamster cells 4 (XRCC4), transcript variant 1, mRNA," Nov. 4, 2010, 4 pages.
GenBank® GI No. 213972635 GenBank® Accession No. NM_001141980, "*Homo sapiens* tumor protein p53 binding protein 1 (TP53BP1), transcript variant 1, mRNA," Nov. 15, 2010, 6 pages.
GenBank® GI No. 213972636 GenBank® Accession No. NP_001135452, "tumor suppressor p53-binding protein 1 isoform 1 [*Homo sapiens*]," Nov. 15, 2010, 3 pages.

(Continued)

*Primary Examiner* — Raymond Henley, III
(74) *Attorney, Agent, or Firm* — Fish & Richardson P.C.

(57) ABSTRACT

This document provides methods and materials involved in assessing responsiveness to PARP inhibitors and platinating agents. For example, methods and materials for using levels of non-homologous end-joining pathway members (e.g., artemis mRNA or polypeptide levels, Ku80 mRNA or polypeptide levels, or DNA-PKcs mRNA or polypeptide levels) to determine if cancer cells that are homologous recombination-deficient are likely to be susceptible or resistant to PARP inhibitors and platinating agents are provided.

19 Claims, 21 Drawing Sheets

(56) References Cited

OTHER PUBLICATIONS

GenBank® GI No. 237757283 GenBank® Accession No. NM_007294, "*Homo sapiens* breast cancer 1, early onset (BRCA1), transcript variant 1, mRNA," Nov. 4, 2010, 8 pages.

GenBank® GI No. 24234690 GenBank® Accession No. NP_005581, "double-strand break repair protein MRE11A isoform 2 [*Homo sapiens*]," Nov. 14, 2010, 3 pages.

GenBank® GI No. 4503841 GenBank® Accession No. NP_001460.1, "X-ray repair cross-complementing protein 6 [*Homo sapiens*]," Nov. 10, 2010, 3 pages.

GenBank® GI No. 4507945 GenBank® Accession No. NP_003392, "DNA repair protein XRCC4 isoform 1 [*Homo sapiens*]," Nov. 4, 2010, 3 pages.

GenBank® GI No. 51093847 GenBank® Accession No. NM_001469, "*Homo sapiens* X-ray repair complementing defective repair in Chinese hamster cells 6 (XRCC6), mRNA," Nov. 20, 2011, 6 pages.

GenBank® GI No. 56550106 GenBank® Accession No. NM_005590, "*Homo sapiens* MRE11 meiotic recombination 11 homolog A (*S. cerevisiae*) (MRE11A), transcript variant 2, mRNA," Nov. 14, 2010, 5 pages.

GenBank® GI No. 6552299 GenBank® Accession No. NP_009225, "breast cancer type 1 susceptibility protein isoform 1 [*Homo sapiens*]," Nov. 4, 2010, 3 pages.

GenBank® GI No. 71902539 GenBank® Accession No. NM_000051, "*Homo sapiens* ataxia telangiectasia mutated (ATM), mRNA," Nov. 12, 2010, 12 pages.

GenBank® GI No. 71902540 GenBank® Accession No. NP_000042, "serine-protein kinase ATM [*Homo sapiens*]," Nov. 12, 2010, 3 pages.

GenBank® GI No. 73765544 GenBank® Accession No. NP_000305, "phosphatidylinositol-3,4,5-trisphosphate 3-phosphatase and dual-specificity protein phosphatase PTEN [*Homo sapiens*]," Nov. 14, 2010, 3 pages.

GenBank® GI No. 76496496 GenBank® Accession No. NM_001033855, "*Homo sapiens* DNA cross-link repair 1C (DCLRE1C), transcript variant a, mRNA," Nov. 10, 2010, 5 pages.

GenBank® GI No. 76496497 GenBank® Accession No. NP_001029027, "protein artemis isoform a [*Homo sapiens*]," Nov. 10, 2010, 3 pages.

Gottipati et al., "Poly(ADP-ribose) polymerase is hyperactivated in homologous recombination-defective cells," *Cancer Res.*, 70(13):5389-5398, Jul. 2010.

Hashimoto et al., "Mutagenic activity of topoisomerase I inhibitors," *Clin. Cancer Res.*, 1:369-376, Apr. 1995

Hickson et al., "Identification and characterization of a novel and specific inhibitor of the ataxia-telangiectasia mutated kinase ATM," *Cancer Res.*, 64(24):9152-9159, Dec. 2004.

Hingorani et al., "Inhibition of repair of radiation-induced DNA damage enhances gene expression from replication-defective adenoviral vectors," *Cancer Res.*, 68(23):9771-9778, Dec. 2008.

Hochegger et al., "Parp-1 protects homologous recombination from interference by Ku and Ligase IV in vertebrate cells," *EMBO J.*, 25(6):1305-1314, Epub Feb. 2006.

Kameoka et al., "RNA interference directed against Poly(ADP-Ribose) polymerase 1 efficiently suppresses human immunodeficiency virus type 1 replication in human cells.," *J. Virol.*, 78(16):8931-8934, Aug. 2004.

Katsube et al., "Differences in sensitivity to DNA-damaging Agents between XRCC4- and Artemis-deficient human cells," *J Radiat Res.*, 52(4):415-424, 2011.

Kaufmann et al., "Altered formation of topotecan-stabilized topoisomerase I-DNA adducts in human leukemia cells," *Blood*, 89(6):2098-2104, Mar. 1997.

Kaufmann, "Reutilization of immunoblots after chemiluminescent detection," *Anal. Biochem.*, 296(2):283-286, Sep. 2001

Löser et al., "Sensitization to radiation and alkylating agents by inhibitors of poly(ADP-ribose) polymerase is enhanced in cells deficient in DNA double-strand break repair," *Mol Cancer Ther.* 9(6):1775-1787, Jun. 2010.

Lou et al., "MDC1 regulates DNA-PK autophosphorylation in response to DNA damage," *J. Biol. Chem.*, 279(45):46359-46362, Nov. 2004.

Luo et al., "A new XRCC1-containing complex and its role in cellular survival of methyl methanesulfonate treatment," *Mol. Cell. Biol.*, 24(19):8356-8365, Oct. 2004.

Ma et al., "Hairpin opening and overhang processing by an Artemis/DNA-dependent protein kinase complex in nonhomologous end joining and V(D)J recombination," *Cell*, 108(6):781-794, Mar. 2002.

Mendes-Pereira et al., "Synthetic lethal targeting of PTEN mutant cells with PARP inhibitors," *EMBO Mol. Med.*, 1:315-322, Sep. 2009.

Nimura et al., "Silencing Ku80 using small interfering RNA enhanced radiation sensitivity in vitro and in vivo," *Int. J. Oncol.*, 30(6):1477-1484, Jun. 2007.

Patel et al., "Nonhomologous end joining drives poly(ADP-ribose) polymerase (PARP) inhibitor lethality in homologous recombination-deficient cells," and "Supporting Information," *Proc Natl Acad Sci U S A.*, 108(8):3406-3411, Feb. 2011.

Penning et al., "Discovery of the Poly(ADP-ribose) polymerase (PARP) inhibitor 2-[(R)-2-methylpyrrolidin-2-yl]-1H-benzimidazole-4-carboxamide (ABT-888) for the treatment of cancer," *J. Med. Chem.*, 52(2):514-523, print Jan. 2009, Epub Dec. 2008.

Rouleau et al., "PARP inhibition: PARP1 and beyond," *Nat Rev Cancer*, 10(4):293-301, print Apr. 2010, Epub Mar. 2010.

Sakai et al., "Functional restoration of BRCA2 protein by secondary BRCA2 mutations in BRCA2-mutated ovarian carcinoma," *Cancer Res.*, 69(16):6381-6386, Aug. 2009.

Scully et al., "Genetic analysis of BRCA1 function in a defined tumor cell line," *Mol. Cell.*, 4(6):1093-1099, Dec. 1999.

Segovis et al., "PI3K links NKG2D signaling to a CrkL pathway involved in natural killer cell adhesion, polarity, and granule secretion," *J. Immunol.*, 182(11):6933-6942, Jun. 2009.

Seluanov et al., "DNA end joining becomes less efficient and more error-prone during cellular senescence," *Proc. Natl. Acad. Sci. USA*, 101(20):7624-7629, print May 2004, Epub Apr. 2004.

Sourisseau et al., "Aurora-A expressing tumour cells are deficient for homology-directed DNA double strand-break repair and sensitive to PARP inhibition," *EMBO. Mol. Med.*, 2(4):130-142, Apr. 2010

Stiff et al., "ATM and DNA-PK function redundantly to phosphorylate H2AX after exposure to ionizing radiation," *Cancer Res.*, 64(7):2390-2396, Apr. 2004.

The Cancer Genome Atlas Research Network, "Integrated genomic analyses of ovarian carcinoma," *Nature*, 474(7353):609-615, Jun. 2011.

Tomlinson et al., "Characterization of a breast cancer cell line derived from a germ-line BRCA1 mutation carrier," *Cancer Res.*, 58(15):3237-3242, Aug. 1998.

Uematsu et al., "Autophosphorylation of DNA-PKCS regulates its dynamics at DNA double-strand breaks," *J. Cell. Biol.*, 177(2):219-229, Apr. 2007.

Verkaik et al., "Different types of V(D)J recombination and end-joining defects in DNA double-strand break repair mutant mammalian cells," *Eur. J. Immunol.*, 32(3):701-709, Mar. 2002.

Wang et al., "Biochemical evidence for Ku-independent backup pathways of NHEJ," *Nucleic Acids Res.*, 31(18):5377-5388, Sep. 2003.

Wang et al., "PARP-1 and Ku compete for repair of DNA double strand breaks by distinct NHEJ pathways," *Nucleic Acids Res.*, 34(21):6170-6182, Epub Nov. 2006.

Waninger et al., "Identification of cellular cofactors for human immunodeficiency virus replication via a ribozyme-based genomics approach," *J. Virol.*, 78(23):12829-12837, Dec. 2004.

Weston et al., "The PARP inhibitor olaparib induces significant killing of ATM-deficient lymphoid tumor cells in vitro and in vivo," *Blood*, 116(22):4578-4587, Nov. 2010.

Weterings and Chen, "The endless tale of non-homologous end-joining," *Cell Res.*, 18(1):114-124, Jan. 2008.

Williamson et al., "ATM deficiency sensitizes mantle cell lymphoma cells to poly(ADP-ribose) polymerase-1 inhibitors," *Mol. Canc. Ther.*, 9(2):347-357, Feb. 2010.

Zhang et al., "Artemis is a negative regulator of p53 in response to oxidative stress," *Oncogene*, 28(22): 2196-2204, Jun. 2009.

Ziv et al., "Recombinant ATM protein complements the cellular A-T phenotype," *Oncogene*, 15(2):159-167, Jul. 1997.

_US 8,729,048 B2_

METHODS AND MATERIALS FOR ASSESSING RESPONSIVENESS TO PARP INHIBITORS AND PLATINATING AGENTS

CROSS-REFERENCE TO RELATED APPLICATIONS

This application claims the benefit of U.S. Provisional Application Ser. No. 61/562,735, filed Nov. 22, 2011. The disclosure of the prior application is considered part of (and is incorporated by reference in) the disclosure of this application.

STATEMENT AS TO FEDERALLY SPONSORED RESEARCH

This invention was made with government support under grant numbers CA136393 and GM072474 awarded by the National Institutes of Health. The government has certain rights in the invention.

BACKGROUND

1. Technical Field

This document relates to methods and materials involved in assessing responsiveness to poly(ADP-ribose) polymerase (PARP) inhibitors and platinating agents. For example, this document relates to methods and materials for using levels of non-homologous end-joining (NHEJ) pathway members (e.g., artemis mRNA or polypeptide levels) to determine if cancer cells that are homologous recombination (HR)-deficient are likely to be susceptible or resistant to PARP inhibitors and platinating agents.

2. Background Information

PARP1 is an abundant nuclear enzyme that synthesizes ADP-ribose polymer (pADPr) when activated by DNA nicks or breaks. Activation of PARP1 has important effects on a variety of cellular processes, including base excision repair (BER), transcription, and cellular bioenergetics. The role of PARP1 in the DNA damage response sparked interest in the development of PARP inhibitors as potential chemosensitizers for the treatment of cancer. The more recent observation that PARP inhibition is particularly lethal to cells deficient in HR proteins generated additional excitement in the cancer chemotherapy community. The current explanation for this hypersensitivity focuses on a mechanism in which loss of PARP1 activity is thought to result in accumulation of DNA single-strand breaks (SSBs), which are subsequently converted to DNA double strand breaks (DSBs) by the cellular replication and/or transcription machinery. These DSBs, which are repaired by HR in BRCA-positive cells, are presumed to accumulate in BRCA1- or BRCA2-deficient cells, leading to subsequent cell death. Heightened sensitivity to PARP inhibition has also been observed in cells with other genetic lesions that affect HR, including phosphatase and tensin homolog (PTEN) deficiency (Mendes-Pereira et al., *EMBO Mol. Med.*, 1:315-322 (2009)), ataxia telangiectasia mutated (ATM) deficiency (Williamson et al., *Mol. Canc. Ther.*, 9:347-357 (2010) and Weston et al., *Blood*, 116:4578-4587 (2010)), and Aurora A overexpression (Sourisseau et al., *EMBO Mol. Med.*, 2:130-142 (2010)).

SUMMARY

This document provides methods and materials related to assessing responsiveness to PARP inhibitors and platinating agents. For example, this document provides methods and materials for using one or more levels of NHEJ pathway members (e.g., artemis mRNA or polypeptide levels) to determine if cancer cells that are HR-deficient are likely to be susceptible or resistant to PARP inhibitors and platinating agents. As described herein, HR-deficient cancer cells (e.g., HR-deficient ovarian cancer cells) that have an NHEJ pathway that is intact or elevated are likely to be susceptible to treatment with PARP inhibitors and platinating agents, while HR-deficient cancer cells that have an NHEJ pathway that is inactive or reduced are likely to be resistant to treatment with PARP inhibitors and platinating agents.

Determining if a mammal (e.g., a human patient) has HR-deficient cancer cells with an intact or elevated NHEJ pathway can allow physicians and the patient, in the case of humans, to determine a course of treatment that involves one or more PARP inhibitors and/or one or more platinating agents that is appropriate for that patient. For example, a patient found to have HR-deficient ovarian cancer cells with an intact NHEJ pathway can be treated with one or more PARP inhibitors and/or one or more platinating agents. Likewise, determining if a mammal (e.g., a human patient) has HR-deficient cancer cells with an inactive or reduced NHEJ pathway can allow physicians and the patient, in the case of humans, to determine a course of cancer treatment other than PARP inhibitors and platinating agents such as a course of ionizing radiation. For example, a patient found to have HR-deficient ovarian cancer cells with an inactive NHEJ pathway can be treated with ionizing radiation, liposomal doxorubicin, or gemcitabine.

In some cases, the methods and materials provided herein can be used to determine a patient's likelihood of experiencing cancer progression-free survival. For example, HR-deficient cancer cells from a patient can be examined to determine whether the cancer cells have an NHEJ pathway that is intact or elevated or an NHEJ pathway that is inactive or reduced. The presence of an intact or elevated NHEJ pathway can, at least in part, indicate that the cancer patient is likely to experience prolonged progression-free survival, while the presence of an inactive or reduced NHEJ pathway can, at least in part, indicate that the cancer patient is likely to experience cancer progression.

In general, one aspect of this document features a method for treating cancer. The method comprises, or consist essentially of, (a) detecting the absence of a reduced level of functionality of a non-homologous end-joining pathway in homologous recombination-deficient cancer cells from a mammal having cancer, and (b) administering, to the mammal, a PARP inhibitor or platinating agent under conditions wherein the number of viable cancer cells within the mammal is reduced. The cancer cells can be ovarian or breast cancer cells. The mammal can be a human. The detecting step can comprise detecting the absence of a reduced level expression of an artemis mRNA or polypeptide. The method can comprise administering the PARP inhibitor to the mammal. The PARP inhibitor can be Iniparib, Olaparib, Veliparib, or Rucaparib. The method can comprise administering the platinating agent to the mammal. The platinating agent can be cisplatin, carboplatin, or oxaliplatin. The homologous recombination-deficient cancer cells can be BRCA1-deficient cancer cells. The homologous recombination-deficient cancer cells can be BRCA2-deficient cancer cells. The homologous recombination-deficient cancer cells can be ATM-deficient cancer cells.

In another aspect, this document features a method for treating cancer. The method comprises, or consist essentially of, (a) detecting the presence of a reduced level of functionality of a non-homologous end-joining pathway in homologous recombination-deficient cancer cells from a mammal having cancer, and (b) administering, to the mammal, a cancer treatment agent other than a PARP inhibitor or platinating agent under conditions wherein the number of viable cancer cells within the mammal is reduced. The cancer cells can be ovarian or breast cancer cells. The mammal can be a human. The detecting step can comprise detecting the presence of a reduced level expression of an artemis mRNA or polypeptide. The method can comprise administering paclitaxel, topotecan, temozolmide, or gemcitabine to the mammal. The homologous recombination-deficient cancer cells can be BRCA1-deficient cancer cells. The homologous recombination-deficient cancer cells can be BRCA2-deficient cancer cells. The homologous recombination-deficient cancer cells can be ATM-deficient cancer cells.

In another aspect, this document features a method for assessing responsiveness to a PARP inhibitor or platinating agent treatment. The method comprises, or consists essentially of, (a) determining whether or not homologous recombination-deficient cancer cells from a mammal have a reduced level of functionality of a non-homologous end-joining pathway, (b) classifying the cancer cells as likely to be resistant to treatment with a PARP inhibitor or platinating agent if the cancer cells have the reduced level, and (c) classifying the cancer cells as likely to be susceptible to treatment with a PARP inhibitor or platinating agent if the cancer cells do not have the reduced level. The cancer cells can be ovarian or breast cancer cells. The mammal can be a human. The determining step can comprise determining whether or not the cancer cells express a reduced level of an artemis mRNA or polypeptide. The method can comprise assessing responsiveness to the PARP inhibitor treatment, wherein the PARP inhibitor treatment is an Iniparib treatment, an Olaparib treatment, a Veliparib treatment, or a Rucaparib treatment. The method can comprise assessing responsiveness to the platinating agent treatment, wherein the platinating agent treatment is a cisplatin treatment, a carboplatin treatment, or an oxaliplatin treatment. The homologous recombination-deficient cancer cells can be BRCA1-deficient cancer cells. The homologous recombination-deficient cancer cells can be BRCA2-deficient cancer cells. The method of claim 1, wherein the homologous recombination-deficient cancer cells can be ATM-deficient cancer cells.

In another aspect, this document features a method for assessing responsiveness to a PARP inhibitor or platinating agent treatment. The method comprises, or consists essentially of, (a) detecting the presence of a reduced level of functionality of a non-homologous end-joining pathway in homologous recombination-deficient cancer cells from a mammal, and (b) classifying the cancer cells as likely to be resistant to treatment with a PARP inhibitor or platinating agent based at least in part on the presence.

In another aspect, this document features a method for assessing responsiveness to a PARP inhibitor or platinating agent treatment. The method comprises, or consists essentially of, (a) detecting the absence of a reduced level of functionality of a non-homologous end-joining pathway in homologous recombination-deficient cancer cells from a mammal, and (b) classifying the cancer cells as likely to be susceptible to treatment with a PARP inhibitor or platinating agent based at least in part on the absence.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

Figure 11:
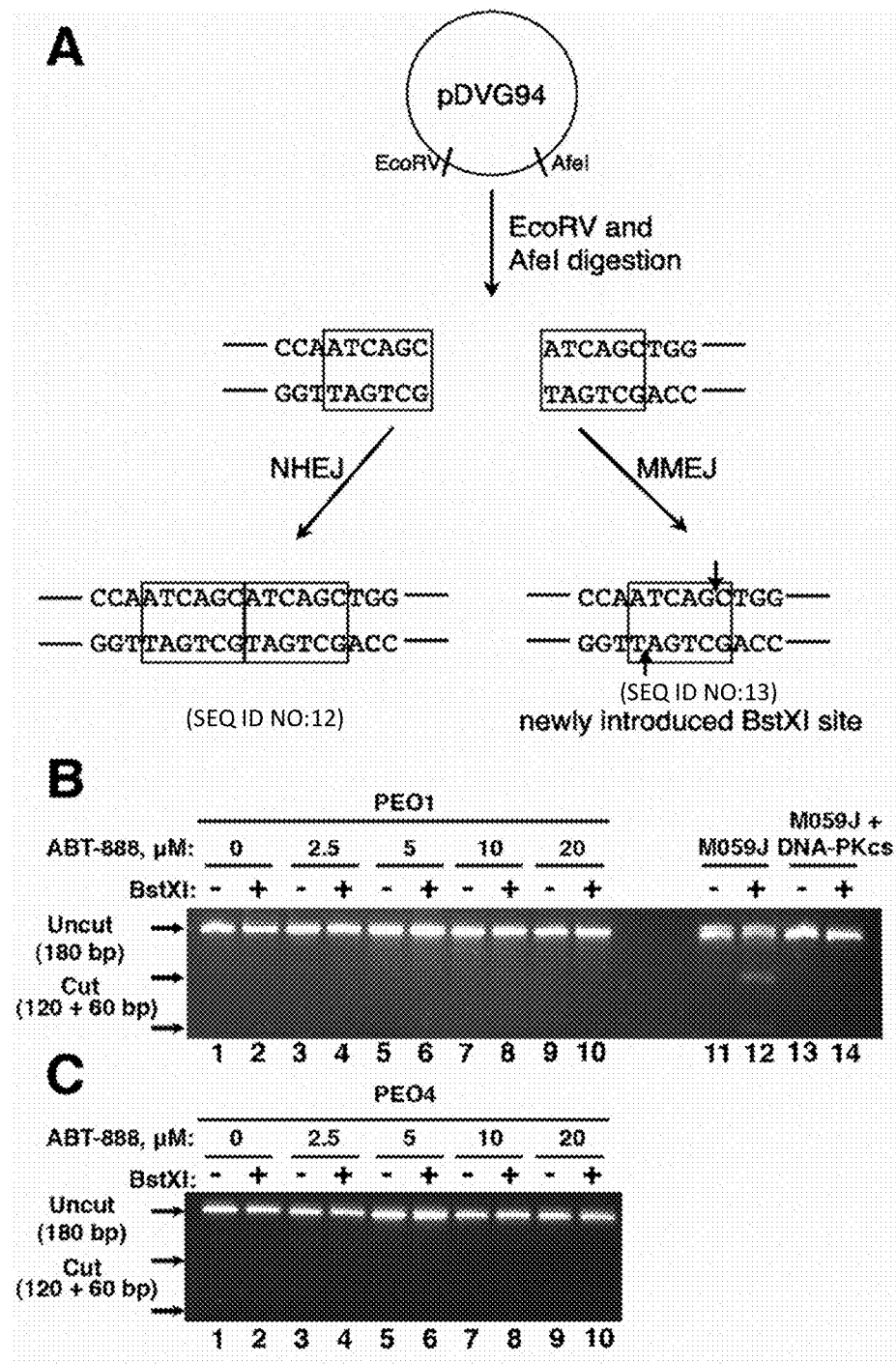

Successfully recircularized plasmid will produce intact EGFP, which can be assayed via flow cytometry. Any residual uncut plasmid, due to the insertion of the Ad2 exon within the EGFP open reading frame, will be EGFP negative. A pCherry plasmid was co-transfected with substrate to correct for transfection efficiency. (B) and (C) Quantitation of NHEJ activity in PEO1 and PEO4 cells transfected with HindIII substrate (B) or I-SceI substrate (C) and exposed to ABT-888 for 72 hours. Each data point represents the mean±SEM from 3 independent experiments. Representative flow cytometry profiles are shown in FIG. 11.

Figure 4:
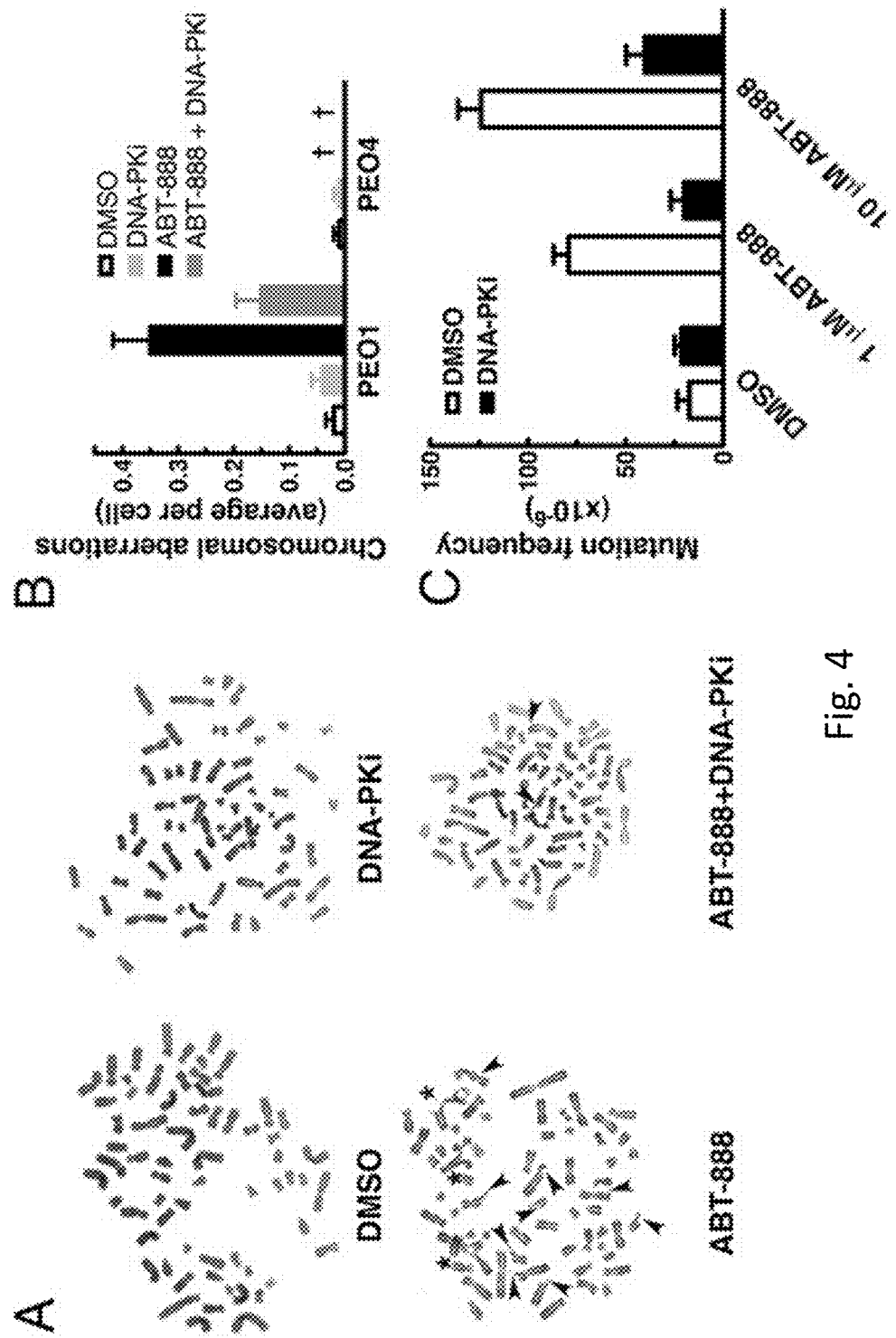

FIG. 4. PARP inhibitor-induced chromosomal derangement and genomic instability is dependent on DNA-PK activity. (A) Representative images of metaphase spreads from cells treated with diluent (0.2% DMSO), 500 nM DNA-PKi, 2.5 µM ABT-888, or both ABT-888 and DNA-PKi for 72 hours. Chromosomal breaks are marked with arrowheads and radial structures are marked with asterisks. (B) Quantitation of data from (A) showing average radial chromosomes per cell (n=100 for each data point pooled from two separate experiments, error bars represent SEM). † indicate values that are zero. (C) Calculated mutagenesis frequency in BRCA2-mutant CAPAN1 cells after control treatment or exposure to ABT-888 with or without 250 nM DNA-PKi. Each bar represents the mean±SEM of 5-8 plates. This result is representative of 3 independent experiments.

Figure 5:
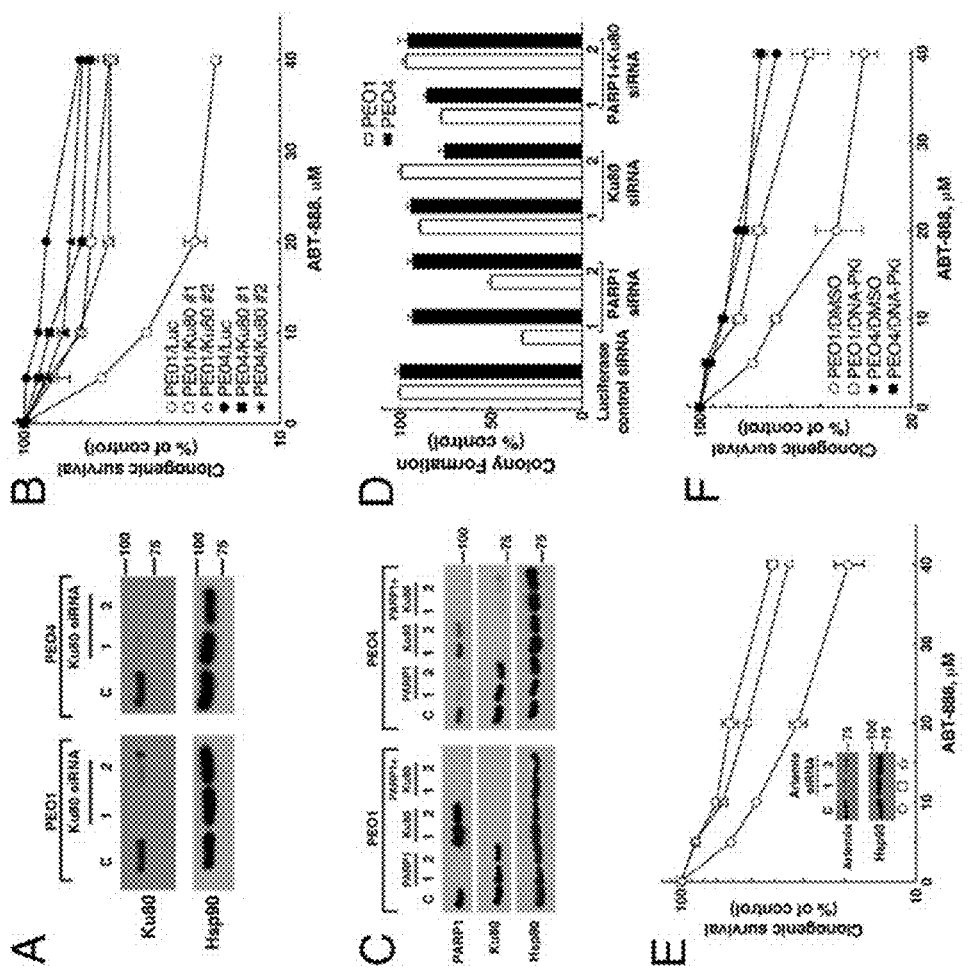

FIG. 5. NHEJ is a major contributor to PARP inhibitor effects in BRCA2-deficient cells. (A) Western blots showing knockdown of Ku80 in PEO1 and PEO4 cells. (B) Clonogenic survival of PEO1 and PEO4 cells from (A), which were treated with the indicated ABT-888 concentration for 72 hours, washed, and allowed to form colonies. (C) Western blots following treatment with siRNA targeting luciferase (control), Ku80, PARP1, or both Ku80 and PARP1. (D) Clonogenic viability of PEO 1 and PEO4 cells from (C). Following knockdown, cells were plated onto triplicate plates and allowed to form colonies. (E) Clonogenic survival of PEO1 cells following Artemis knockdown. After treatment with the indicated siRNA, plates were treated with indicated concentration of ABT-888 for 72 hours, washed, and allowed to form colonies. Inset, Western blots showing knockdown using luciferase (control) or Artemis siRNAs in PEO1 cells. (F) Clonogenic survival of PEO1 and PEO4 cells treated for 72 hours with ABT-888 in combination with diluent or 500 nM DNA-PKi. All results are reported as means of triplicate plates±SEM, and are representative of 3 independent experiments.

Figure 6:
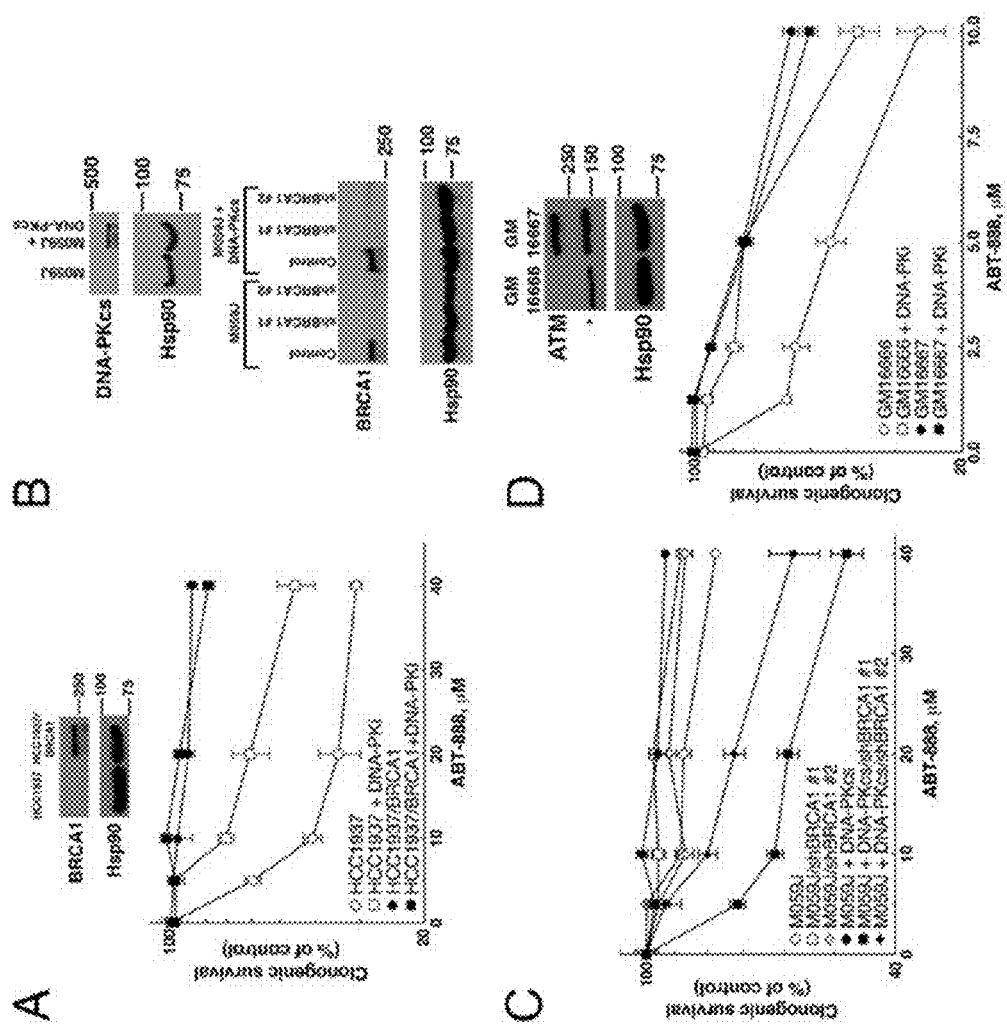

FIG. 6. NHEJ contributes to PARP inhibitor induced effects in other HR-deficient contexts. (A) BRCA1-deficient HCC1937 and BRCA1-reconstituted HCC1937/BRCA1 cells were continuously exposed to ABT-888 in the presence or absence of 125 nM DNA-PKi and assayed for clonogenic survival. Inset, Western blots of cell lysates from HCC1937 and HCC1937/BRCA1. (B) Western blots of M059J and reconstituted M059J+DNA-PKcs lines showing the restoration of DNA-PK expression and the shRNA-mediated knockdown of BRCA1. (C) Clonogenic survival of shRNA transfected M059J/M059J+DNA-PKcs lines treated with ABT-888 for 72 hours. (D) Clonogenic survival of ATM-deficient GM16666 or ATM-reconstituted GM16667 fibroblasts. Cells were exposed to ABT-888 for 48 hours in the presence or absence of 250 nM DNA-PKi, washed, and allowed to form colonies. Inset, Western blots of lysates from GM16666 and GM16667 fibroblasts. Data is displayed as mean±SEM of triplicate plates. Results are representative of 3 independent experiments.

Figure 7:
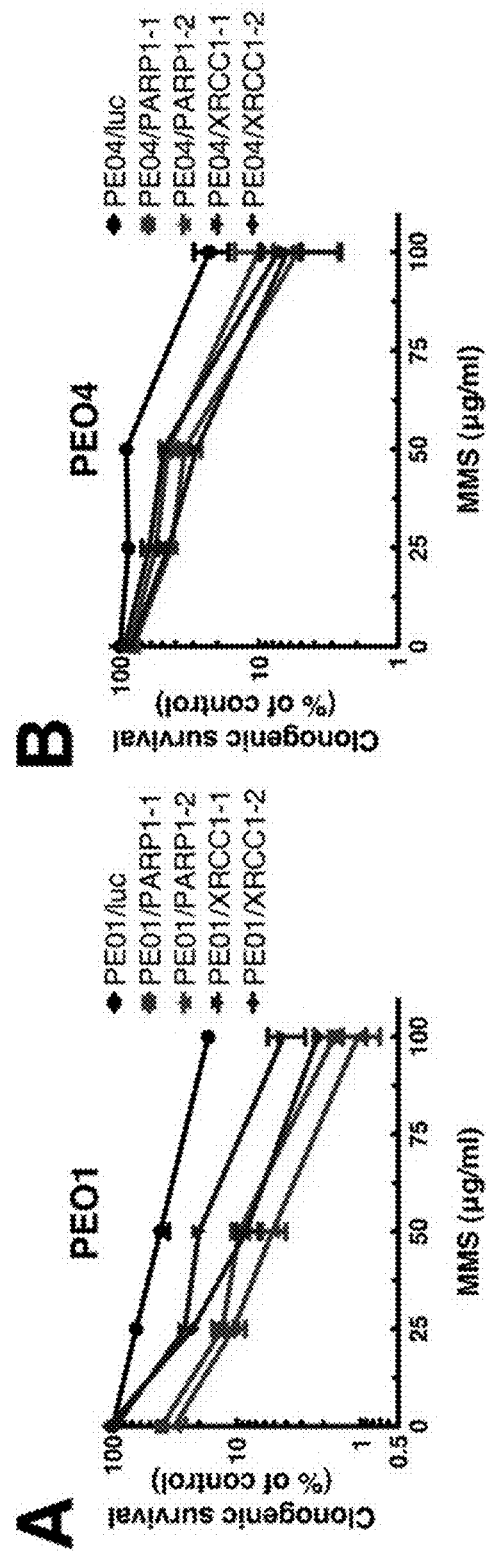

FIG. 7. siRNA knockdown of PARP1 or XRCC1 induces a BER defect. MMS clonogenic survival curves of PEO1 cells (A) or PEO4 cells (B) following siRNA-directed knockdown of luciferase (control), PARP1, or XRCC1. Following knockdown, cells were plated, allowed to adhere, and treated with the indicated concentration of MMS for 1 hour. The plates were then washed and allowed to form colonies in drug-free medium. Results are reported as mean±SEM of triplicate plates. Results are representative of 3 independent experiments.

Figure 2:
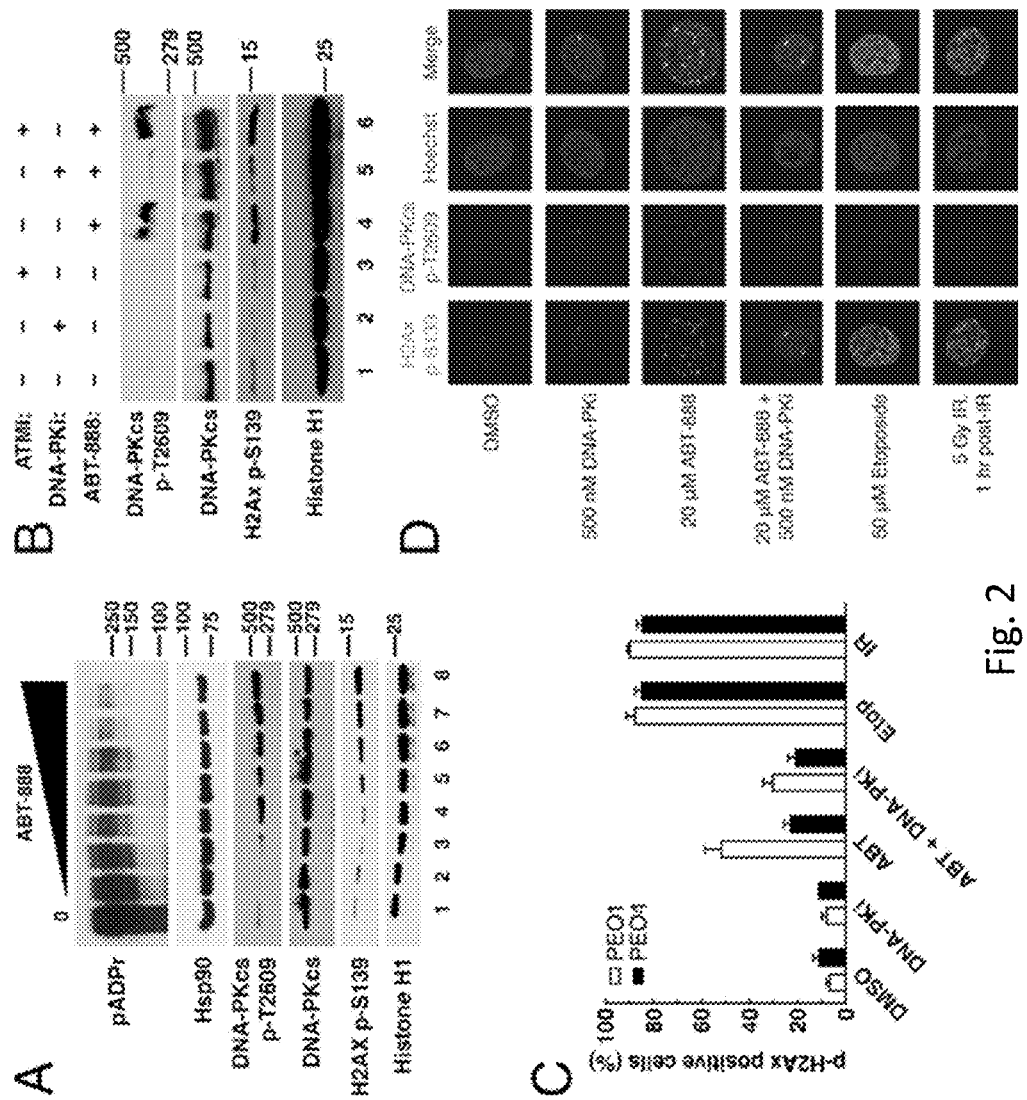
FIG. 2. DNA-PK is activated following PARP inhibitor exposure in PEO1 cells. (A) Western blots for poly(ADP-ribose) polymer (pADPr) and phosphorylation of DNA-PK substrates (DNA-PKcs autophosphorylation at $Thr^{2609}$ and Histone H2AX at $Ser^{139}$) in PEO1 cells following 72 hours exposure to increasing concentrations of ABT-888 (0, 0.625, 1.25, 2.5, 5, 10, 20, and 40 µM). Hsp90, total DNA-PKcs, and Histone H1 are used as loading controls. (B) Phosphorylation of DNA-PK substrates after treatment for 72 hours with diluent (0.2% DMSO, lanes 1 and 4), 500 nM DNA-PK inhibitor AZ12594248 (DNA-PKi, lanes 2 and 5), or 5 µM ATM inhibitor KU55933 (ATMi, lanes 3 and 6) alone (lanes 1-3) or in combination with 20 µM ABT-888 (lanes 4-6). (C) Quantitation of cells positive for phospho-H2AX foci in PEO1 and PEO4 cells, following treatment with DMSO, 500 nM DNA-PKi, 20 µM ABT-888 (ABT), ABT-888 and DNA-PKi, 50 µM Etoposide (Etop), or 5 Gy ionizing radiation (IR). Cells were exposed to ABT-888 and/or DNA-PKi for 72 hours, etoposide for 1 hour, or allowed to recover for 1 hour after IR. Results are reported as mean±SEM of 3 independent experiments. (D) Confocal images of PEO1 cells treated as in (D). Phospho-$Ser^{139}$-H2AX is shown in green, phospho-$Thr^{2609}$-DNA-PKcs in red, and Hoechst 33258 in blue.
Figure 8:
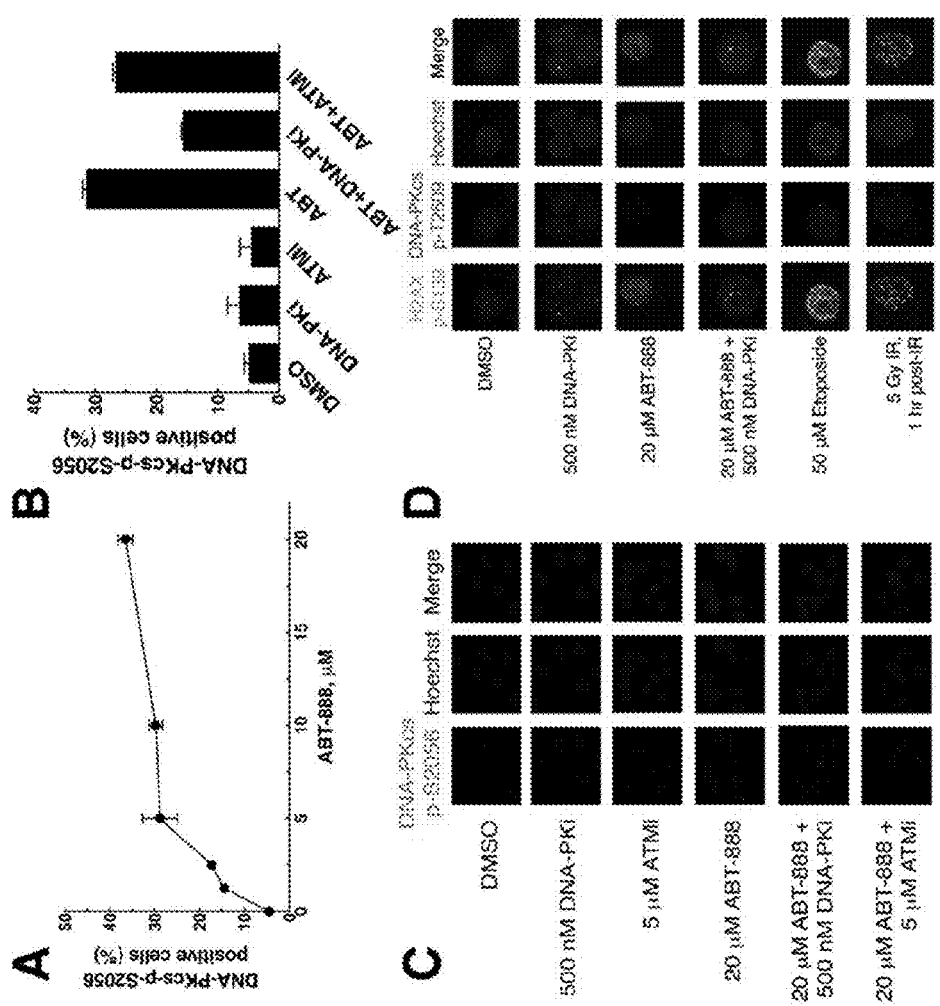

FIG. 8. PARP inhibition induces phosphorylation of DNA-PKcs selectively in PEO1 cells. (A) Quantitation of PEO1 cells positive for phospho-Ser$^{2056}$ DNA-PKcs foci following 72 hours exposure to increasing concentrations of ABT-888. (B) Quantitation of PEO1 cells positive for phospho-Ser$^{2056}$ DNA-PKcs foci following 72 hours exposure to diluent (0.2% DMSO), 500 nM DNA-PKi, 5 µM ATMi alone (columns 1-3) or with 20 µM ABT-888 (columns 4-6). (C) Representative confocal images of PEO1 cells from (B). (D) Confocal images of PEO4 cells treated as indicated in FIG. 2D. Phospho-H2AX is shown in green, phospho-Thr$^{2609}$ DNA-PKcs in red, and Hoechst 33258 in blue. Results in (A) and (B) are presented as means±SEM of 3 independent experiments.

Figure 9:
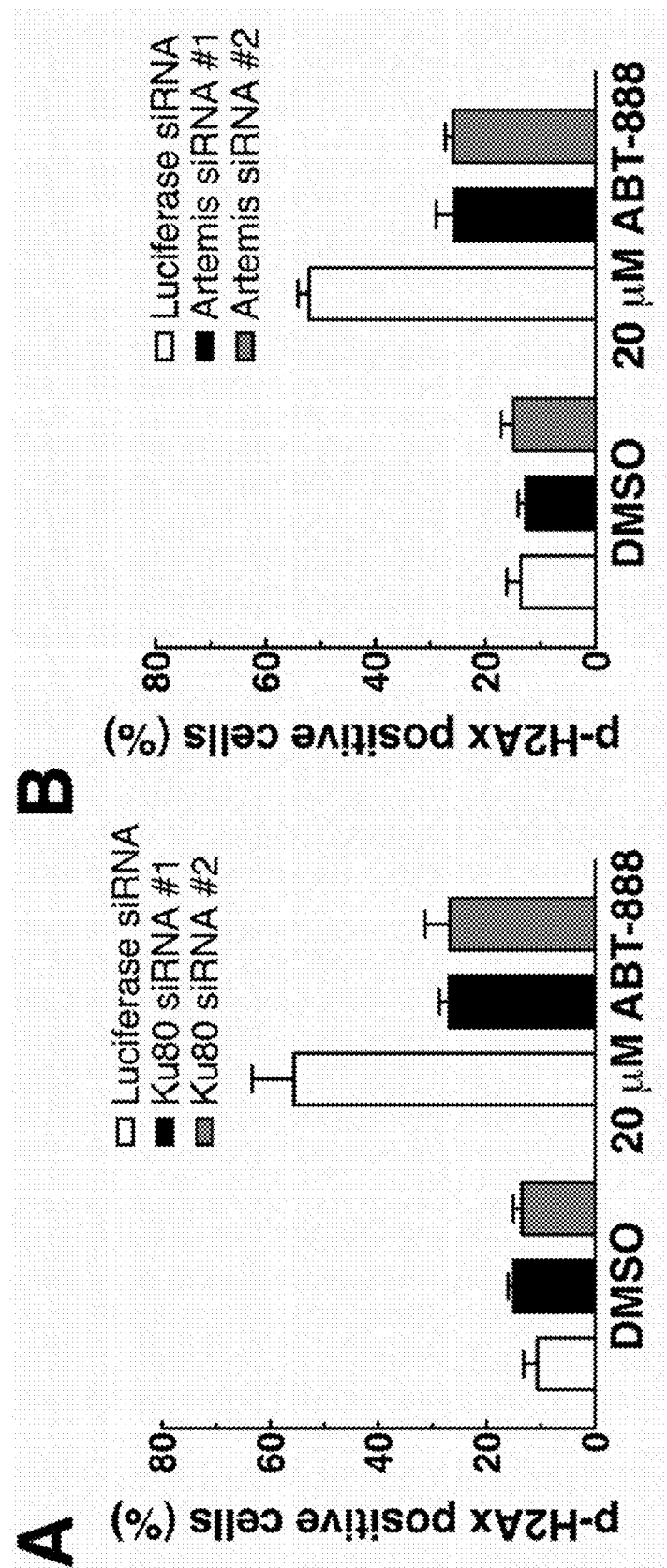

FIG. 9. siRNA-mediated knockdown of NHEJ components reduces ABT-888 induced formation of phospho-H2AX foci. PEO1 cells, following siRNA-mediated knockdown of Ku80 (A) or Artemis (B), were exposed to either diluent (0.1% DMSO) or 20 µM ABT-888 for 72 hours, fixed, and stained for phospho-H2AX foci. Positive nuclei were defined as having >10 foci. Results are presented as means±SEM of 3 independent experiments.

Figure 10:
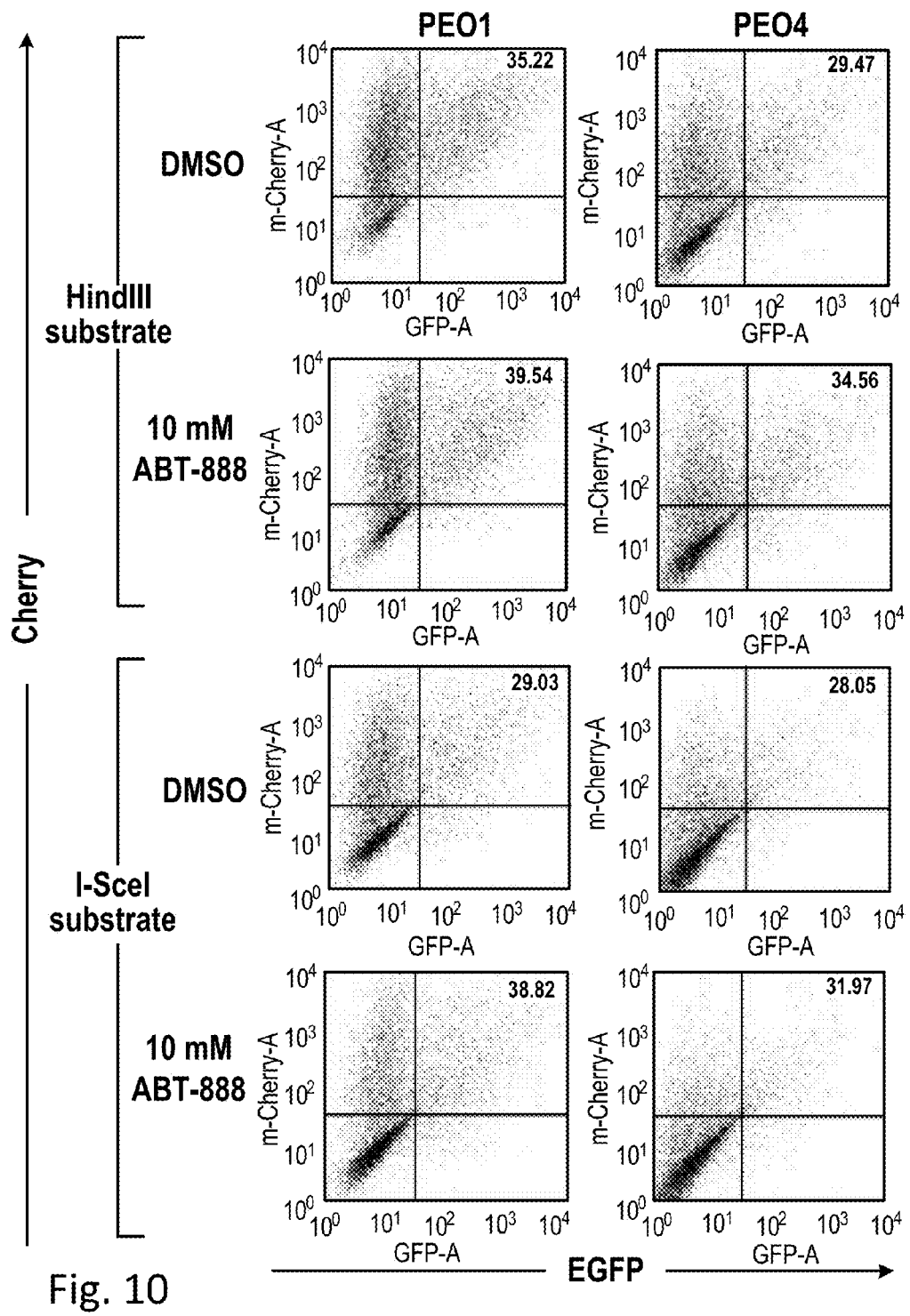

FIG. 10. ABT-888 induces NHEJ as measured by an in vivo substrate assay. Representative dot plots of PEO1 (left) or PEO4 (right) cells that were assayed for end-joining by flow microfluorimetry. Cells were transfected with HindIII-linearized Pem1-Ad2-EGFP (top two rows) or I-SceI-linearized Pem1-Ad2-EGFP (bottom two rows), and exposed to either DMSO or 10 µM ABT-888 for 72 hours. The number of double positive (EGFP$^+$Cherry$^+$) cells relative to total Cherry-positive cells was calculated to determine end-joining The percentage of transfected cells expressing repaired plasmid is shown in the upper right-hand corner of each plot.

FIG. 11. PARP inhibition fails to induce microhomology-mediated end-joining (MMEJ). (A) Schematic of the reporter substrate used to assay for MMEJ activity. Cleavage of pDVG94 with EcoRV and AfeI creates a blunt-ended linearized substrate, with identical 6-bp ends. Direct joining by NHEJ will result in maintenance of both repeats, but MMEJ will excise one repeat, introducing a new BstXI site. PCR across recircularized substrate produces a product of 180 bp, which can be cut into 120 and 60 bp fragments if the BstXI site was created. This figure is adapted from a figure provided elsewhere (Verkaik et al., *Eur. J. Immunol.*, 32:701-709 (2002)). (B) and (C) Agarose gel from a representative MMEJ assay. PEO1 (B, lanes 1-10) and PEO4 (C) cells were treated with increasing concentrations of ABT-888 following transfection with linearized pDVG94. The size of the initial PCR product (180 bp) as well as BstXI cleaved products (120 bp and 60 bp) are indicated. As a positive and negative control, a cell line previously documented to undergo MMEJ (Lou et al., *J. Biol. Chem.*, 279:46359-46362 (2004)), M059J (B, lanes 11 and 12), and a MMEJ-negative line, M059J+DNA-PKcs (B, lanes 13 and 14) were used. Images were captured from one gel and cut to create two panels.

Figure 12:
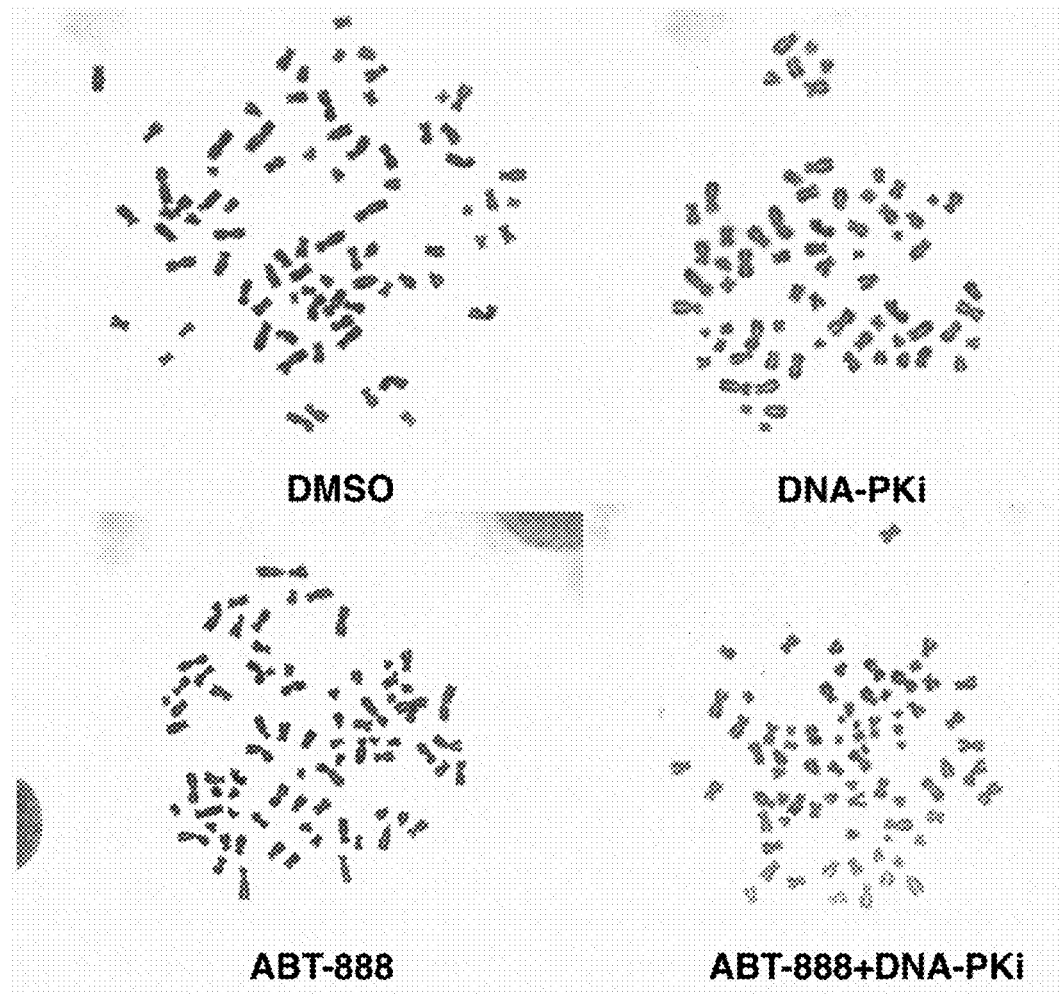

FIG. 12. PARP inhibition fails to induce chromosomal instability in BRCA2-positive PEO4 cells. Representative metaphase spreads from PEO4 cells treated with 0.2% DMSO, 500 nM DNA-PKi, 2.5 µM ABT-888, or both DNA-PKi and ABT-888.

Figure 13:
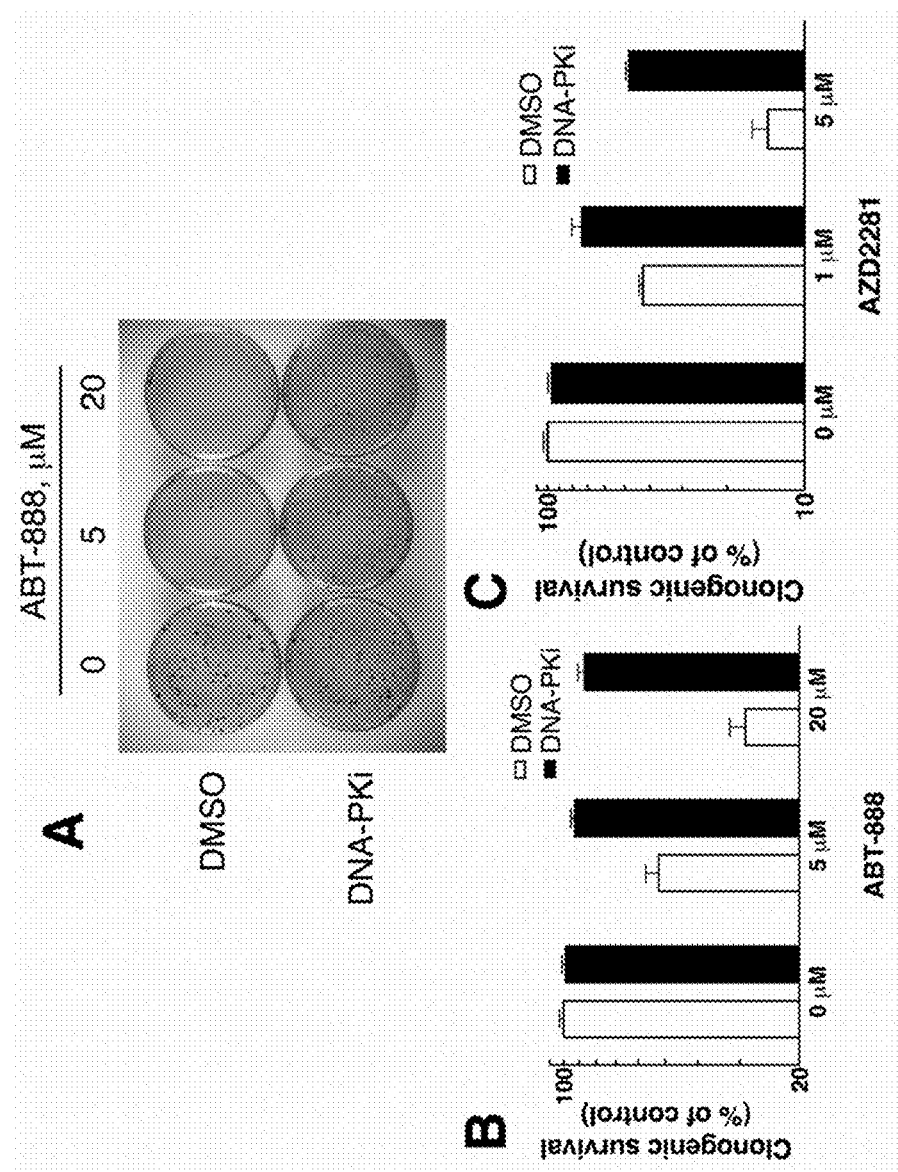

FIG. 13. DNA-PK inhibition diminishes the lethality of multiple PARP inhibitors in PEO1 cells. (A) Representative clonogenic plates after PEO1 cells were treated with ABT-888 (0, 5, or 20 µM) with or without 500 nM DNA-PKi. (B, C) Bar graphs comparing clonogenic survival of PEO1 cells exposed to two PARP inhibitors with or without 500 nM DNA-PKi. The PARP inhibitors used for these assays are ABT-888 (B) and AZD2281/olaparib (C). Results are reported as mean±SEM of triplicate plates.

Figure 14:
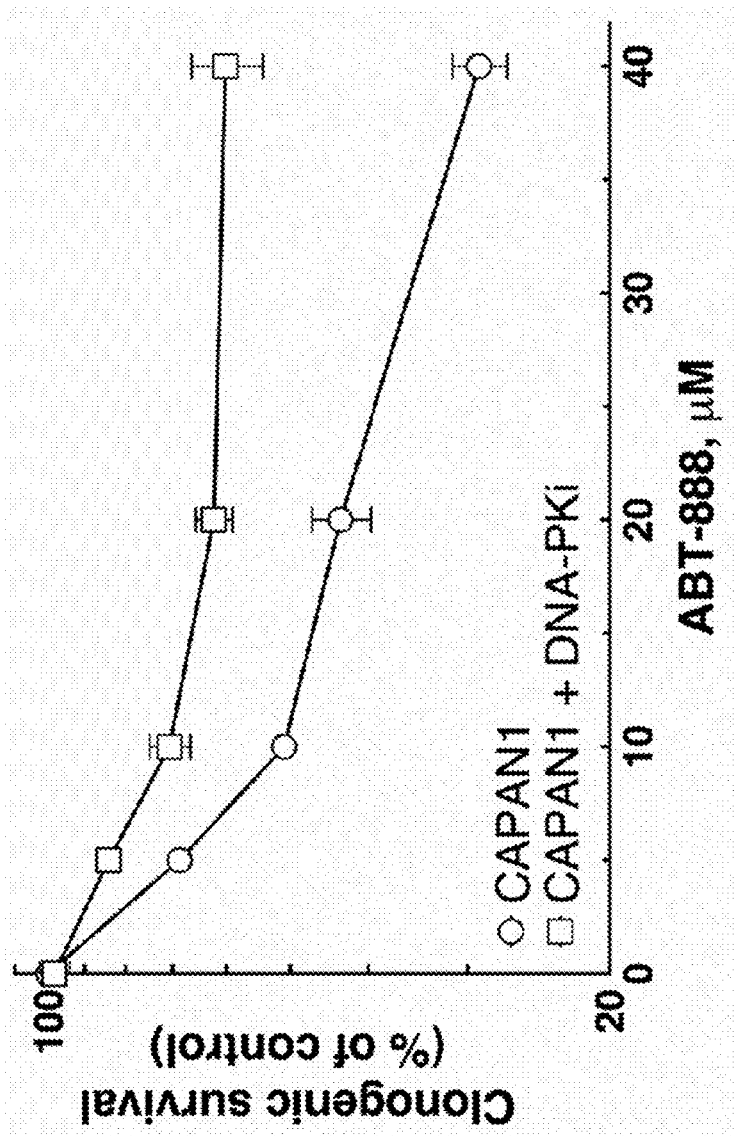

FIG. 14. PARP inhibitor sensitivity of BRCA2-mutant CAPAN1 cells is diminished by DNA-PK inhibition. Clonogenic survival curve of CAPAN-1 cells treated with increasing concentrations of ABT-888 with or without 250 nM DNA-PKi.

Figure 15:
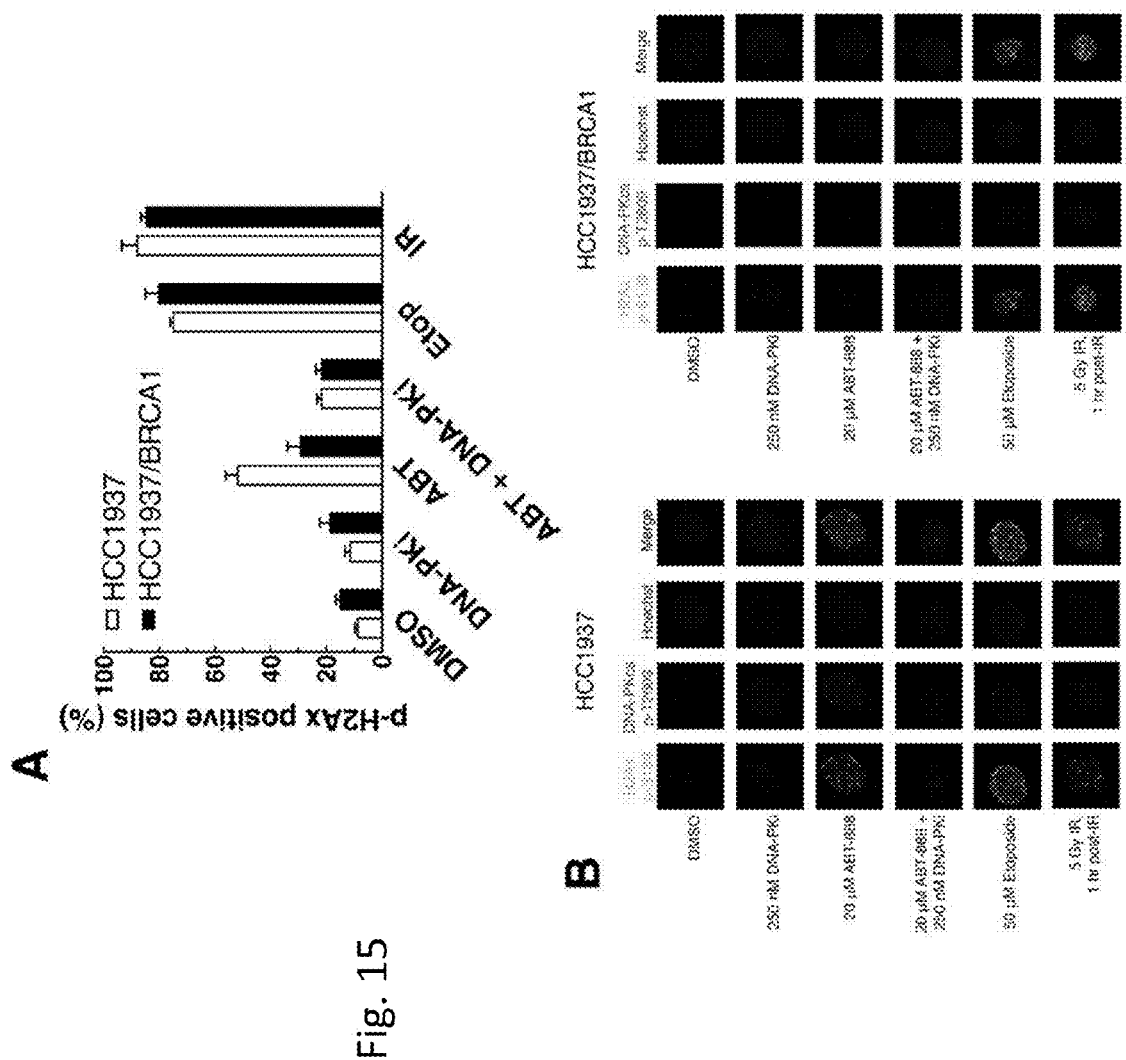

FIG. 15. Upon PARP inhibition, HCC1937 cells form phospho-H2AX foci that colocalize to regions of activated DNA-PK. (A) Quantitation of cells positive for phospho-H2AX foci in HCC1937 and HCC1937/BRCA1 cells, following treatment with 0.2% DMSO, 250 nM DNA-PKi, 20 µM ABT-888 (ABT), ABT-888 and DNA-PKi, 50 µM etoposide (Etop), or 5 Gy ionizing radiation (IR). Cells were exposed to ABT-888 and/or DNA-PKi for 72 hours, etoposide for 1 hour, or allowed to recover 1 hour post-IR. Results are reported as mean±SEM of 3 independent experiments. (B) Confocal microscopy after staining with antibodies to phospho-H2AX (Ser$^{139}$) and phospho-DNA PKcs (Thr$^{2609}$) as in FIG. 2D. HCC1937 cells are shown on the left, and reconstituted HCC1937/BRCA1 cells on the right.

Figure 16:
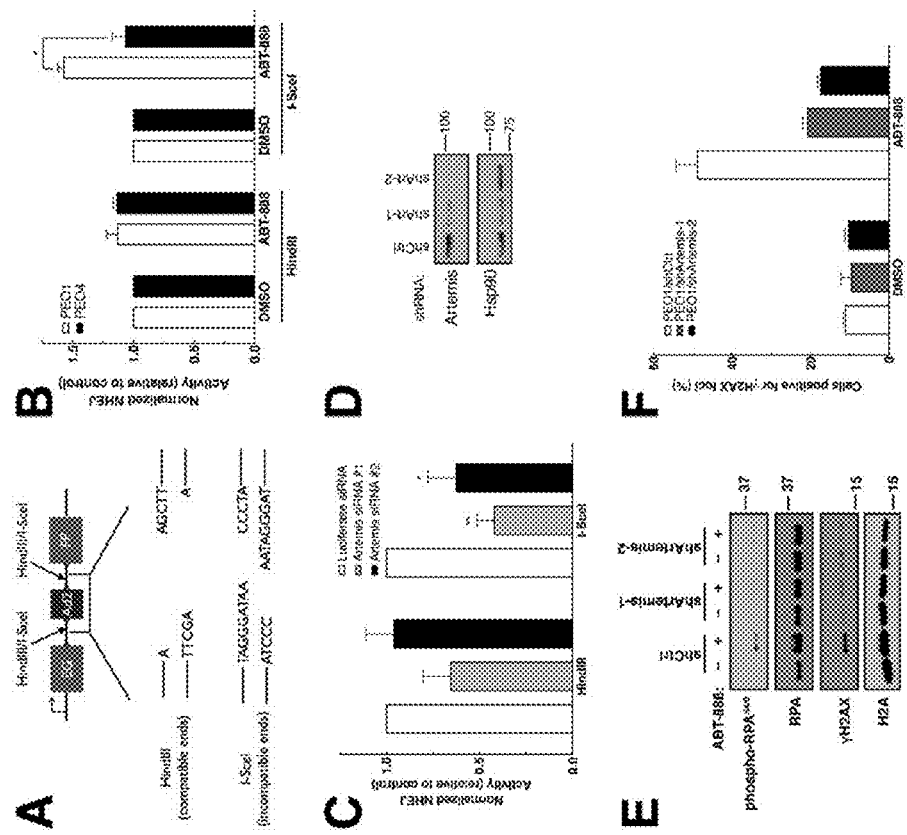

FIG. 16. Resection-dependent NHEJ through Artemis activates the DNA damage response in PEO1 cells treated with PARP inhibitors. (A) Schematic of the NHEJ substrate assay. Schematic of the in vivo NHEJ assay. Pem1-Ad2-EGFP is an EGFP-containing vector with a 2.4 kb intron (Pem1) and one exon (Ad2) inserted into the EGFP cassette. Pem1-Ad2-EGFP was cut with either HindIII or I-SceI to produce linearized substrate with compatible overhangs or incompatible inverted overhangs, respectively. Successfully recircularized plasmid will produce intact EGFP, which can be assayed via flow cytometry. Any residual uncut plasmid, due to the insertion of the Ad2 exon within the EGFP open reading frame, will be EGFP negative. A pCherry plasmid was co-transfected with substrate to correct for transfection efficiency. (B) Quantitation of NHEJ activity in PEO1 and PEO4 cells treated with DMSO or ABT-888 for 72 hours. (C) PEO1 cells were transiently transfected with control (luciferase) or Artemis siRNAs and assayed for NHEJ activity. (D) Stable knockdown of Artemis in PEO1 cells. (E) Phosphorylation of RPA and H2AX in PEO1 shCtrl and PEO1 shArtemis lines treated with DMSO or ABT-888. (F) Graph plotting cells positive for γH2AX foci. Results are reported as means±SEM of 3 independent experiments.

Figure 17:
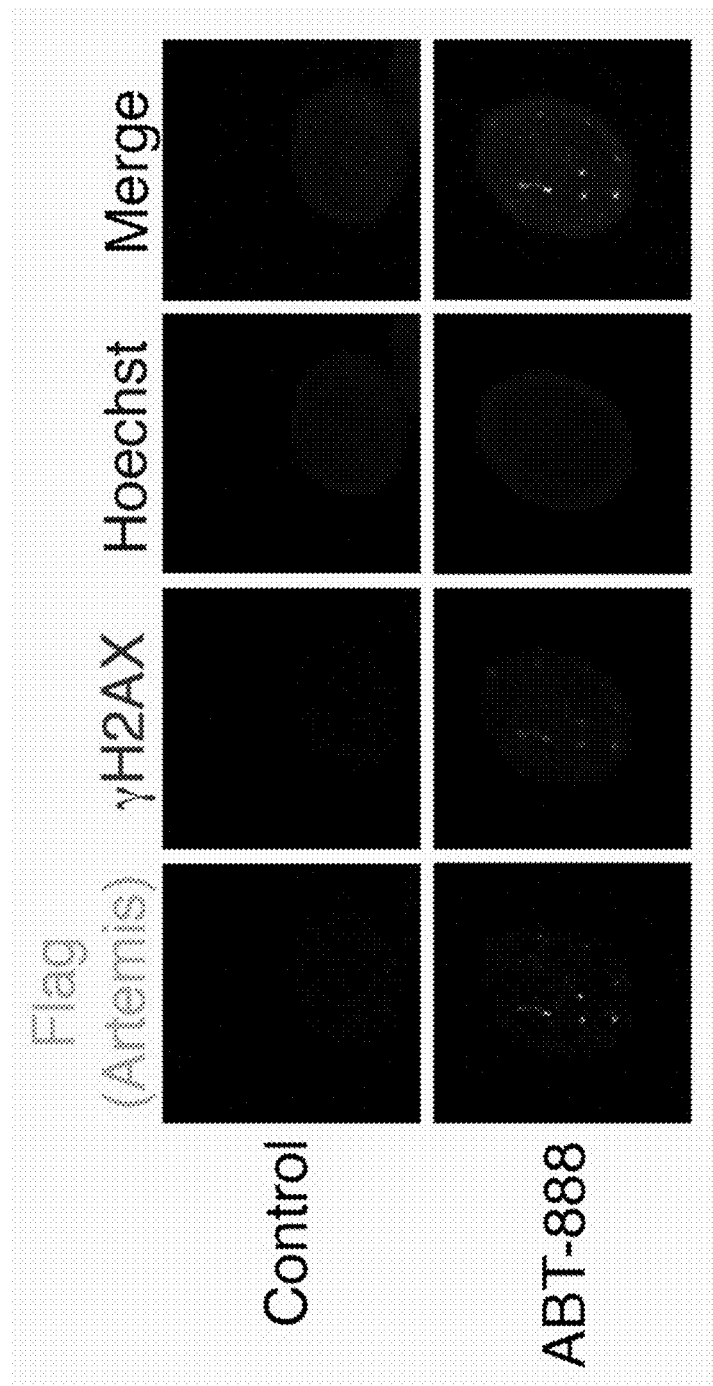

FIG. 17. Artemis is located at sites of DNA damage induced by a PARP inhibitor. PEO1 cells were transiently transfected with Artemis-Flag, treated with diluent or 20 micromolar ABT-888 for 24 hours, and immunostained for Flag tag and gamma-H2AX. Flag staining was evident in green, and gamma-H2AX was evident in red.

Figure 18:
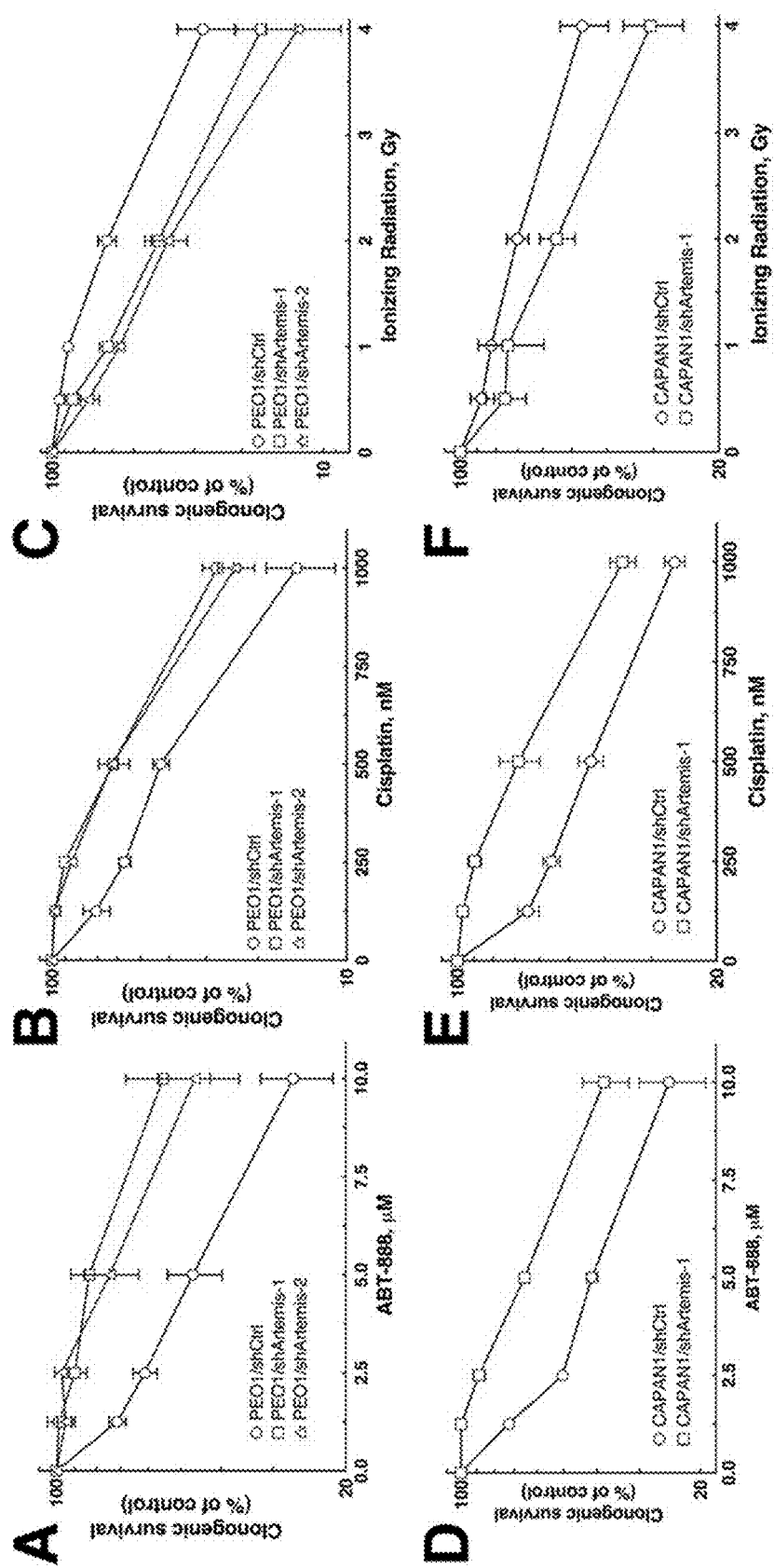

FIG. 18. Artemis knockdown confers resistance to PARP inhibition and cisplatin in BRCA2-deficient/mutant cells. Clonogenic survival assays of PEO1 shRNA lines continuously exposed to ABT-888 (A) or cisplatin (B), or exposed to ionizing radiation (C). (D-F) Clonogenic survival assays of CAPAN1 shRNA lines exposed to ABT-888 (D), cisplatin (E), or exposed to ionizing radiation (F).

Figure 19:
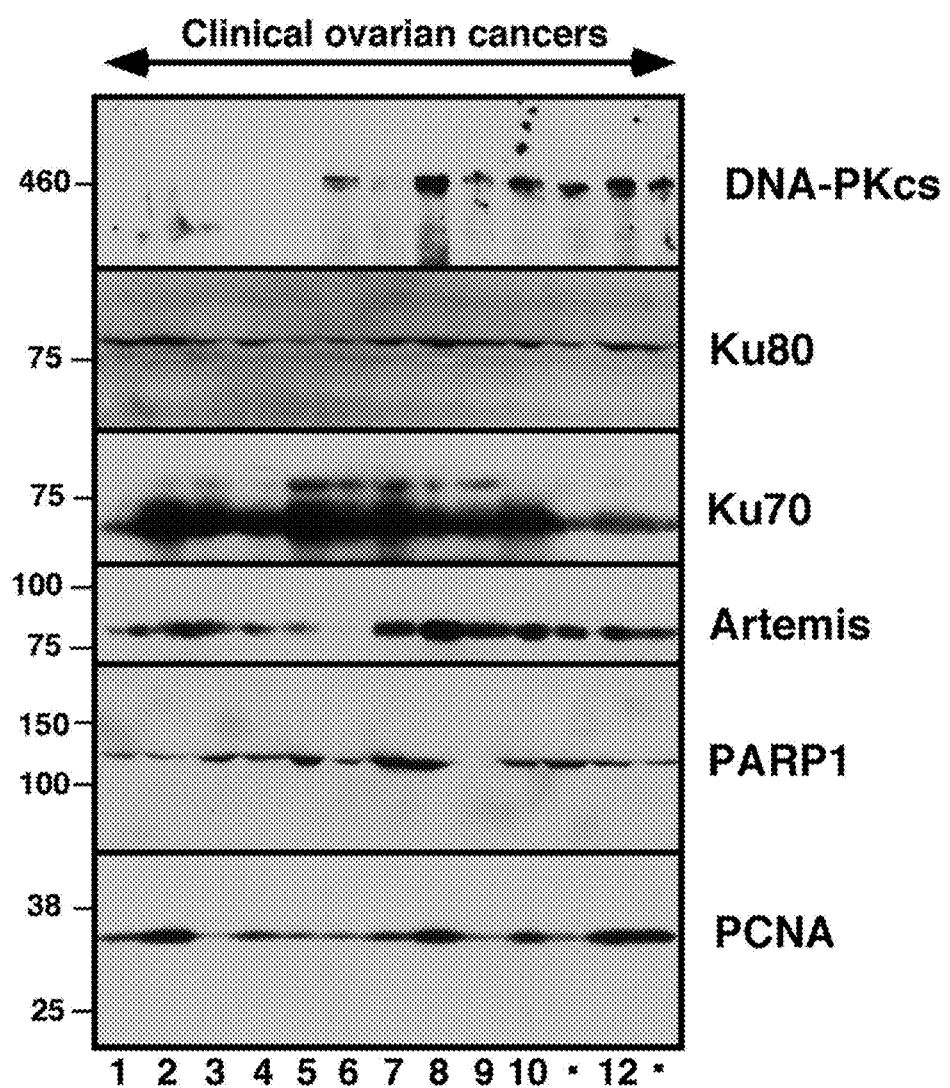

FIG. 19. Variation in NHEJ pathway components at the protein level. Aliquots containing 50 micrograms of protein isolated from 13 separate ovarian cancers arising in patients with BRCA1 or BRCA2 mutations were subjected to SDS-polyacrylamide gel electrophoresis followed by immunoblotting for the indicated antigens. Levels of several of the NHEJ pathway components were observed to be low in some tumors, including DNA-PKcs (low in tumors 1-5 and 7), Ku70 (low in tumors 11 and 13), and artemis (low in tumor 6).

Figure 20:
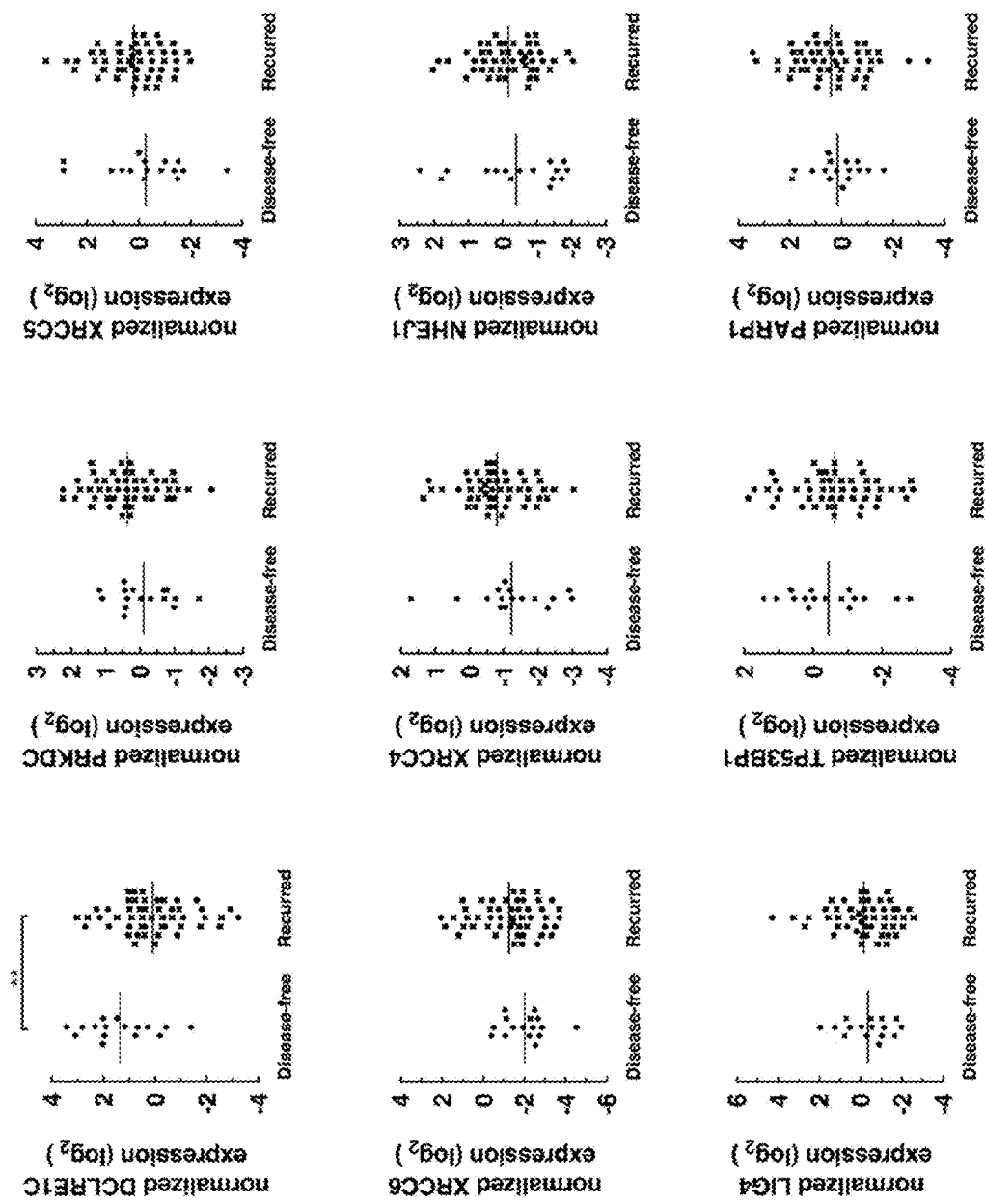

FIG. 20. Comparison of the expression of NHEJ and DNA repair factors in BRCA-mutant patients with sustained remission and patients with recurrences. Expression data from The Cancer Genome Atlas (TCGA) from BRCA-mutant ovarian cancer patients was obtained to compare the expression of NHEJ factors (DCLRE1C, PRKDC, XRCC5, XRCC6, XRCC4, NHEJ1, LIG4) and other repair factors (TP53BP1 and PARP1) between patients who experience disease-free remission and those that experience recurrences.

Figure 21:
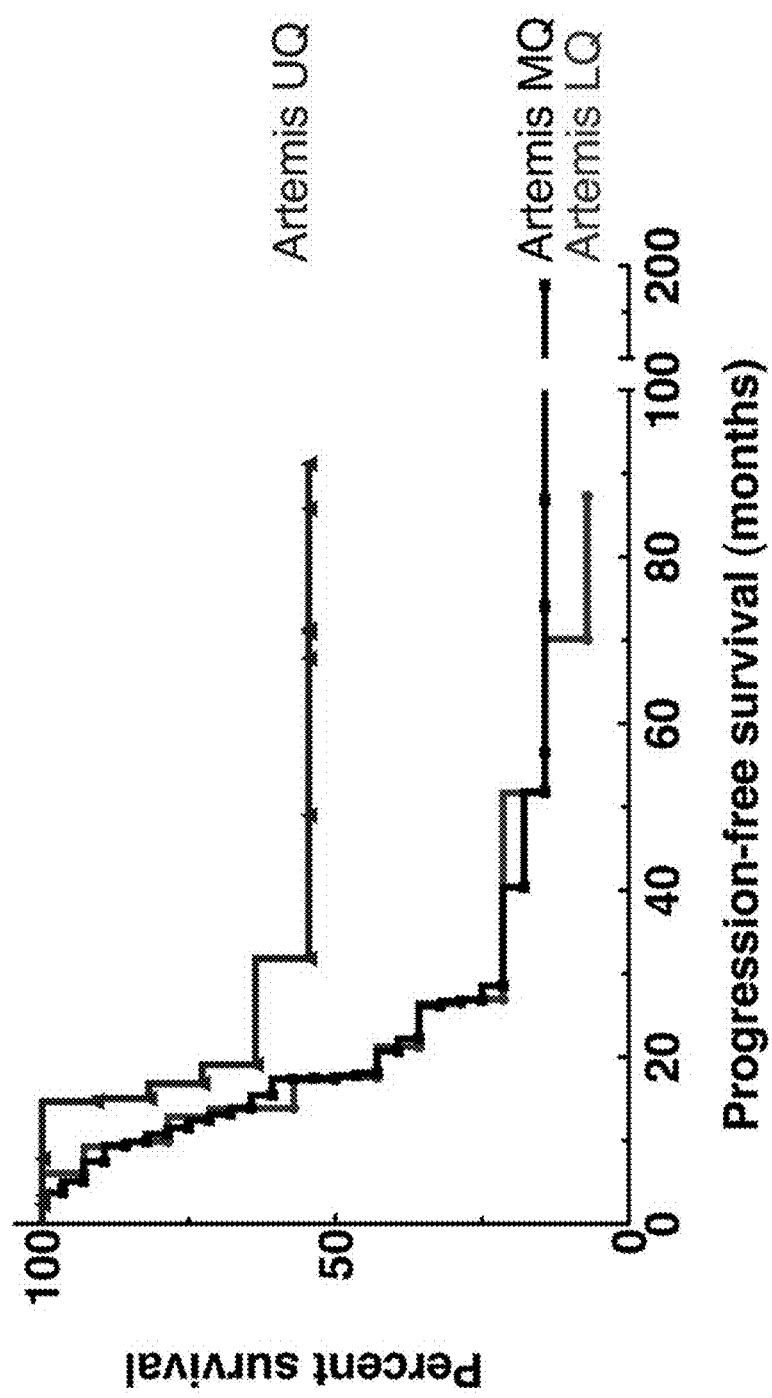

FIG. 21. BRCA-mutant patients expressing high Artemis levels experience sustained progression-free survival. Ovarian cancer patients with BRCA-mutations were segregated into Artemis low-, mid- and high-expressing groups based on expression in the lower quartile (LQ), middle two quartiles (MQ), or upper quartile (UQ), and evaluated for progression-free survival.

DETAILED DESCRIPTION

This document provides methods and materials related to assessing responsiveness to PARP inhibitors and platinating agents. For example, this document provides methods and materials for using one or more levels of NHEJ pathway members (e.g., artemis mRNA or polypeptide levels) to determine if cancer cells that are HR-deficient are likely to be susceptible or resistant to PARP inhibitors and platinating agents. As described herein, HR-deficient cancer cells (e.g., HR-deficient ovarian cancer cells) that have an NHEJ pathway that is intact or elevated are likely to be susceptible to treatment with PARP inhibitors and platinating agents, while HR-deficient cancer cells that have an NHEJ pathway that is inactive or reduced are likely to be resistant to treatment with PARP inhibitors and platinating agents.

Any appropriate HR-deficient cancer cell can be assessed for a functional NHEJ pathway to determine if the mammal's cancer is susceptible to treatment with PARP inhibitors and platinating agents. For example, HR-deficient ovarian, breast, pancreatic, prostate, endometrial, or non-small cell lung cancer cells as well as chronic lymphocytic leukemia or non-Hodgkins lymphoma cells can be assessed for a functional NHEJ pathway to determine if such cells are susceptible to treatment with PARP inhibitors and platinating agents. In addition, the methods and materials provided herein can be used to assess HR-deficient cancer cells from any appropriate mammal For example, HR-deficient cancer cells from a human, monkey, horse, dog, cat, cow, pig, mouse, or rat can be assessed for a functional NHEJ pathway to determine if the cancer cells are susceptible to treatment with PARP inhibitors and platinating agents.

In some cases, the expression level of one or more NHEJ pathway members can be assessed to determine whether HR-deficient cancer cells have (a) an intact or elevated NHEJ pathway or (b) an inactive or reduced NHEJ pathway. One example of an NHEJ pathway member is an artemis polypeptide. The amino acid sequence of a human artemis polypeptide is set forth in GenBank® GI No. 76496496 (GenBank® Accession No. NM_001033855), and the nucleic acid sequence encoding a human artemis polypeptide is set forth in GenBank® GI No. 76496497 (GenBank® Accession No. NP_001029027). Additional amino acid and nucleic acid sequences for artemis polypeptides from other species can be obtained from GenBank® by performing standard sequence searches (e.g., BLAST searches) using the above listed sequences (e.g., a human artemis amino acid or nucleic acid sequence).

Other NHEJ pathway members that can be used as described herein include, without limitation, 53BP1 polypeptides, Ku80 polypeptides, Ku70 polypeptides, Ligase IV polypeptides, DNA-PKcs polypeptides, XLF/Cernunnos polypeptides, and XRCC4 polypeptides. The amino acid sequence of a human 53BP1 polypeptide is set forth in GenBank® GI No. 213972636 (GenBank® Accession No. NP_001135452), and the nucleic acid sequence encoding a human 53BP1 polypeptide is set forth in GenBank® GI No. 213972635 (GenBank® Accession No. NM_001141980). The amino acid sequence of a human Ku80 polypeptide is set forth in GenBank® GI No. 10863945 (GenBank® Accession No. NP_066964), and the nucleic acid sequence encoding a human Ku80 polypeptide is set forth in GenBank® GI No. 195963391 (GenBank® Accession No. NM_021141). The amino acid sequence of a human Ku70 polypeptide is set forth in GenBank® GI No. 4503841 (GenBank® Accession No. NP_001460.1), and the nucleic acid sequence encoding a human Ku70 polypeptide is set forth in GenBank® GI No. 51093847 (GenBank® Accession No. NM_001469). The amino acid sequence of a human Ligase IV polypeptide is set forth in GenBank® GI No. 148539894 (GenBank® Accession No. NP_001091738), and the nucleic acid sequence encoding a human Ligase IV polypeptide is set forth in GenBank® GI No. 148539893 (GenBank® Accession No. NM_001098268). The amino acid sequence of a human DNA-PKcs polypeptide is set forth in GenBank® GI No. 126032350 (GenBank® Accession No. NP_001075109), and the nucleic acid sequence encoding a human DNA-PKcs polypeptide is set forth in GenBank® GI No. 126032349 (GenBank® Accession No. NM_001081640). The amino acid sequence of a human XLF/Cernunnos polypeptide is set forth in GenBank® GI No. 13376142 (GenBank® Accession No. NP_079058.1), and the nucleic acid sequence encoding a human XLF/Cernunnos polypeptide is set forth in GenBank® GI No. 187607429 (GenBank® Accession No. NM_024782). The amino acid sequence of a human XRCC4 polypeptide is set forth in GenBank® GI No. 4507945 (GenBank® Accession No. NP_003392), and the nucleic acid sequence encoding a human XRCC4 polypeptide is set forth in GenBank® GI No. 196162694 (GenBank® Accession No. NM_003401).

Any appropriate method can be used to determine the level of polypeptide or mRNA expression of a NHEJ pathway member. For example, RT-PCR, quantitative PCR, Northern blotting, and gene expression profiling techniques can be used to assess artemis mRNA levels. In some cases, ELISAs, immunocytochemistry, flow cytometry, Western blotting, proteomic, and mass spectrometry techniques can be used to assess artemis polypeptide levels. Any appropriate sample containing cancer cells can be obtained and assessed for expression of a NHEJ pathway member (e.g., artemis expression). For example, fine-needle aspiration biopsies, surgical tissue biopsies, or blood samples can be obtained, and the level of artemis expression within the cancer cells of such samples can be determined as described herein.

The term "reduced level" as used herein with respect to the expression level of a NHEJ pathway member (e.g., artemis) can be in comparison with the median expression level for that NHEJ pathway member that is present in normal non-cancer cells of the same cell type of the cancer to be assessed (e.g., the median artemis expression level determined from a random sampling of 5, 10, 15, 20, 30, 40, 50, 100, 500, or more non-cancer cell samples from humans known not to have cancer) or in comparison to most other cancer cells of the same type of cancer to be assessed (e.g., the median artemis expression level determined from a random sampling of 5, 10, 15, 20, 30, 40, 50 100, 500 or more cancer cell samples from humans who have that particular type of cancer). In such cases, the presence of a reduced level can indicate that the patient's HR-deficient cancer cells are likely to be resistant to treatment with PARP inhibitors and platinating agents, while the absence of such a reduced level (e.g., a normal or elevated level) can indicate that the patient's HR-deficient cancer cells are susceptible to treatment with PARP inhibitors and platinating agents.

The term "HR-deficient cancer cells" as used herein refers to cancer cells that have a reduced ability to carry out homologous recombination. In some cases, HR-deficient cancer cells can be cancer cells lacking a detectable level of homologous recombination. Examples of HR-deficient cancer cells include, without limitation, cancer cells deficient in BRCA1, BRCA2, ATM, MRE11, and/or PTEN. The amino acid sequence of a human BRCA1 polypeptide is set forth in GenBank® GI No. 6552299 (GenBank® Accession No. NP_009225), and the nucleic acid sequence encoding a human BRCA1 polypeptide is set forth in GenBank® GI No. 237757283 (GenBank® Accession No. NM_007294). The amino acid sequence of a human BRCA2 polypeptide is set forth in GenBank® GI No. 119395734 (GenBank® Accession No. NP_000050), and the nucleic acid sequence encoding a human BRCA2 polypeptide is set forth in GenBank® GI No. 119395733 (GenBank® Accession No. NM_000059). The amino acid sequence of a human ATM polypeptide is set forth in GenBank® GI No. 71902540 (GenBank® Accession No. NP_000042), and the nucleic acid sequence encoding a human ATM polypeptide is set forth in GenBank® GI No. 71902539 (GenBank® Accession No. NM_000051). The amino acid sequence of a human MRE11 polypeptide is set forth in GenBank® GI No. 24234690 (GenBank® Accession No. NP_005581), and the nucleic acid sequence encoding a human MRE11 polypeptide is set forth in GenBank® GI No. 56550106 (GenBank® Accession No. NM_005590). The amino acid sequence of a human PTEN polypeptide is set forth in GenBank® GI No. 73765544 (GenBank® Accession No. NP_000305), and the nucleic acid sequence encoding a human PTEN polypeptide is set forth in GenBank® GI No. 110224474 (GenBank® Accession No. NM_000314).

In some cases, the methods and materials provided herein can be used to assess BRCA1-, BRCA2-, and/or ATM-deficient cancer cells. For example, one or more levels of NHEJ pathway members (e.g., artemis mRNA or polypeptide levels) can be used to determine if cancer cells that are BRCA1-deficient are likely to be susceptible or resistant to PARP inhibitors and platinating agents. Examples of PARP inhibitors include, without limitation, Iniparib (previously BSI 201; 4-iodo-3-nitrobenzamide), Olaparib (AZD-2281), Veliparib (ABT-888), Rucaparib (AG 014699), CEP 9722, MK 4827, BMN-673, 3-aminobenzamide, and PJ-34. Examples of platinating agents include, without limitation, cisplatin, carboplatin, oxaliplatin, liposomal cisplatin, satraplatin, picoplatin, and triplatin.

This document also provides methods and materials for treating cancer. For example, a mammal (e.g., a human) having cancer can be assessed as described herein to determine if the mammal has HR-deficient cancer cells (e.g., HR-deficient ovarian or breast cancer cells) that are susceptible to treatment with PARP inhibitors and platinating agents. Once the mammal is identified as having HR-deficient cancer cells that are susceptible to treatment with PARP inhibitors and platinating agents as described herein, one or more PARP inhibitors, one or more platinating agents, or a combination thereof can be administered to the mammal such that the number of viable cancer cells within the mammal is reduced. For example, a mammal identified as having HR-deficient cancer cells with a normal or elevated level of artemis mRNA or artemis polypeptide expression can be treated with a PARP inhibitor, a platinating agent, or a combination thereof.

In some cases, a mammal (e.g., a human) having cancer can be assessed as described herein to determine if the mammal has HR-deficient cancer cells (e.g., HR-deficient ovarian or breast cancer cells) that are resistant to treatment with PARP inhibitors and platinating agents. Once the mammal is identified as having HR-deficient cancer cells that are resistant to treatment with PARP inhibitors and platinating agents as described herein, one or more anti-cancer agents such as paclitaxel, topotecan, temozolmide, or gemcitabine (either alone, in combination, or in combination with a checkpoint inhibitor such as MK-8776) can be administered to the mammal such that the number of viable cancer cells within the mammal is reduced. For example, a mammal identified as having HR-deficient cancer cells with a reduced level of artemis mRNA or artemis polypeptide expression can be treated with paclitaxel, topotecan, temozolmide, or gemcitabine either alone, in combination (e.g. paclitaxel plus topotecan), or in combination with a checkpoint inhibitor such as MK-8776.

This document also provides methods and materials to assist medical or research professionals in determining if HR-deficient cancer cells (e.g., HR-deficient ovarian or breast cancer cells) are susceptible or resistant to treatment with PARP inhibitors and platinating agents. Medical professionals can be, for example, doctors, nurses, medical laboratory technologists, and pharmacists. Research professionals can be, for example, principal investigators, research technicians, postdoctoral trainees, and graduate students. A professional can be assisted by (1) determining the expression level of one or more NHEJ pathway members or the functionality of the NHEJ pathway in cancer cells as described herein, and (2) communicating information about the expression level or functionality to that professional.

Any appropriate method can be used to communicate information to another person (e.g., a professional). For example, information can be given directly or indirectly to a professional. In addition, any type of communication can be used to communicate the information. For example, mail, e-mail, telephone, and face-to-face interactions can be used. The information also can be communicated to a professional by making that information electronically available to the professional. For example, the information can be communicated to a professional by placing the information on a computer database such that the professional can access the information. In addition, the information can be communicated to a hospital, clinic, or research facility serving as an agent for the professional.

The invention will be further described in the following examples, which do not limit the scope of the invention described in the claims.

EXAMPLES

Example 1

Non-Homologous End-Joining Drives PARP Inhibitor Lethality in Homologous Recombination-Deficient Cells Reagents and Antibodies Reagents were purchased from the following companies: ABT-888 (veliparib) and etoposide from Enzo Life Sciences (Plymouth Meeting, Pa.); 6-TG from Sigma-Aldrich (St. Louis, Mo.); and HindIII and I-SceI from New England Biolabs (Ipswich, Mass.). The DNA-PK inhibitor, AZ12594248/KU60648 (a water-soluble analog of NU7441), and ATM inhibitor, KU55933, were kindly provided by KuDOS Pharmaceuticals (Cambridge, UK). Antibodies were purchased or provided as follows: Artemis rabbit polyclonal (Orbigen; San Diego, Calif.); ATM mouse monoclonal 2C1 (Santa Cruz; Santa Cruz, Calif.); BRCA1 rabbit polyclonal and Ku80 rabbit polyclonal (Cell Signaling Technologies; Danvers, Mass.); BRCA2 mouse monoclonal 2B (Calbiochem; San Diego, Calif.); DNA-PKcs mouse monoclonal 42-pcs (Biosource International; Camarillo, Calif.); poly(ADP-ribose) polymer rabbit polyclonal 96-10 and PARP1 mouse monoclonal C2-10 (G. Poirier; Université Laval, Quebec, Calif.); phospho-Ser$^{2056}$ DNA-PKcs rabbit polyclonal (Abcam; Cambridge, Mass.); phospho-Thr$^{2609}$ DNA-PKcs rabbit polyclonal (Z. Lou; Mayo Clinic, Rochester, Minn.); Histone H1 mouse monoclonal (J. Sorace; Veterans Affairs Medical Center, Baltimore, Md.); phospho-Ser$^{139}$ Histone H2AX mouse monoclonal JBW301 (Millipore; Billerica, Mass.); Hsp90b mouse monoclonal (D. Toft; Mayo Clinic, Rochester, Minn.); and XRCC1 rabbit polyclonal (Bethyl Laboratories; Montgomery, Tex.). AZD2281 was obtained from Chemietek (Indianapolis, Ind.).

Cell Culture

PEO1 and PEO4 cells (Sakai et al., *Cancer Res.*, 69:6381-6386 (2009); obtained from F. Couch at Mayo Clinic, Rochester, Minn.) were cultured in DMEM medium containing 10% (v/v) heat-inactivated fetal calf serum (FCS), 100 μM nonessential amino acids, and 10 μg/mL insulin (medium A). BRCA1-deficient HCC1937 and reconstituted HCC1937/BRCA1 cells (Scully et al., *Mol. Cell.*, 4:1093-1099 (1999); obtained from J. Chen at M.D. Anderson Cancer Center, Houston, Tex.) were cultured in RPMI 1640 containing 10% (v/v) FCS (medium B). M059J and M059J+DNA-PKcs cell lines (obtained from L. Karnitz, Mayo Clinic, Rochester, Minn.) were grown in DMEM/F-12 (1:1) medium supplemented with 15% (v/v) FCS (medium C). GM16666 and GM16667 cell lines were purchased from the Coriell Institute (Camden, N.J.) and cultured in DMEM supplemented with 10% (v/v) FCS (medium D) and 100 μg/mL hygromycin. CAPAN1 cells were cultured in RPMI 1640 medium containing 15% (v/v) FCS (medium E). All media contained 100 units/mL penicillin G, 100 μg/mL streptomycin, and 2 mM glutamine.

siRNA/shRNA Transfection

All siRNA oligonucleotides were purchased from Ambion, Inc. (Austin, Tex.). Sequences, with references, are provided below. PEO1 and PEO4 cells were transfected with 150 picomoles of siRNA using the HiPerfect lipid transfection reagent (Qiagen; Valencia, Calif.). On day 1, 8-10×10$^5$ cells were plated onto 6-well dishes in 2.4 mL of antibiotic-free medium and incubated for 24 hours in siRNA-lipid complex (150 picomoles+12 μL HiPerfect in 120 μL sterile RPMI). On day 2, cells were washed with sterile RPMI, and the transfection procedure was repeated. On day 3, cells were trypsinized, replated onto 100-mm tissue culture dishes, and grown in medium A. On day 4, cells were harvested for immunoblotting, immunofluorescence, or clonogenic assays as described below. For short hairpin-mediated knockdown in M059J and M059J+DNA-PKcs cells, 5-10×10$^6$ cells were electroporated at 240 V for 10 ms using a square-wave electroporator (BTX Systems; Holliston, Mass.). Mission shRNA constructs (Sigma-Aldrich) targeting BRCA1 are listed below. Clonogenic assays and protein harvest were performed 48 hours after electroporation.

siRNA Sequences.

The following siRNA sequences were used:

```
Artemis-1:
5'-CUGAAGAGAGCUAGAACAGAA-3' (SEQ ID NO: 1)
(Zhang et al., Oncogene, 28: 2196-2204 (2009))

Artemis-2:
5'-UUAGGAGUCCAGGUUCAUGAA-3' (SEQ ID NO: 2)
(Zhang et al., Oncogene, 28: 2196-2204 (2009))

Ku80-1:
5'-GCGAGUAACCAGCUCAUAAU U-3' (SEQ ID NO: 3)
(Nimura et al., Int. J. Oncol., 30:
1477-1484 (2007))

Ku80-2:
5'-AAGAGCUAAUCCUCAAGUCUU-3' (SEQ ID NO: 4)
(Waninger et al., J. Virol., 78:
12829-12837 (2004))

Luciferase control:
5'-CUUACGCUGAGUACUUCGAUU-3' (SEQ ID NO: 5)

PARP1-1:
5'-AAGCCUCCGCUCCUGAAC AAU-3' (SEQ ID NO: 6)
(Kameoka et al., J. Virol., 78: 8931-8934 (2004))

PARP1-2:
5'-AAGAUAGAGCGUGAAGGCGAA-3' (SEQ ID NO: 7)
(Kameoka et al., J. Virol., 78: 8931-8934 (2004))

XRCC1-1:
5'-AGGGAAGAGGAAGUUGGAUUU-3' (SEQ ID NO: 8)
(Brem and Hall, Nucleic Acids Res., 33:
2512-2520 (2005))

XRCC1-2:
5'-CUCGACUCACUGUGCAGAAUU-3' (SEQ ID NO: 9)
(Luo et al., Mol. Cell. Biol., 24:
8356-8365 (2004))
```

Mission shRNA sequences (Sigma-Aldrich) were as follows:

```
shBRCA1 #1 (Hx72):
5'-CCGGCCCACCTAATTGTACTGAATTCTCGAGA-

ATTCAGTACAAT TAGGTGGGTTTTTG-3' (SEQ ID NO: 10)
and shBRCA1 #2 (Hx75):
5'-CCGG-
CCCTAAGTTTACTTCTCTAAACTCGAGTTTAGAGAA

GTAAACTTAGGGTTTTTG-3'. (SEQ ID NO: 11)
```

NHEJ End-Joining Assay

The end-joining reporter plasmid pEGFP-Pem1-Ad2 described elsewhere (Wang et al., *Nucleic Acids Res.*, 34:6170-6182 (2006); Seluanov et al., *Proc. Natl. Acad. Sci. USA*, 101:7624-7629 (2004); and Fattah et al., *PLoS Genet.*, 6:e1000855 (2010); see also (FIG. 3A)) was provided by E. Hendrickson (University of Minnesota, Minneapolis, Minn.) and was digested with either HindIII or I-SceI for 12 hours, and gel purified using a Qiagen gel extraction kit. Linearized pEGFP-Pem1-Ad2 (4 µg) was co-transfected with 4 mg pCherry by electroporation using a 280 V, 10 ms pulse delivered by a square-wave electroporator. Four hours after electroporation, medium was supplemented with the broad-spectrum caspase inhibitor QVD-OPh at 5 µM (SM Biochemicals, Anaheim, Calif.) in addition to the indicated concentration of ABT-888. After exposure for 72 hours, cells were trypsinized, washed in PBS, and fixed in 2% (w/v) paraformaldehyde in PBS. Flow cytometry was performed on a Becton Dickinson LSR II flow cytometer (BD Biosciences; Franklin Lakes, N.J.). Results were reported as a ratio of double-positive cells (EGFP+Cherry+) to the total number of Cherry-positive cells, to normalize for transfection efficiency.

Cytogenetics

Cell harvest and metaphase slide preparation were performed for metaphase analysis as described elsewhere (Fletcher, *Curr. Protoc. Hum. Genet.*, 2:Unit 10.13. (1994)). Fifty non-banded metaphases from each cell line were analyzed and scored for radial formations as well as major and minor breakage according to the International System of Human Cytogenetic Nomenclature. Images of cells with breakage were captured using a CytoVision Imaging System (Genetix; New Milton, UK).

HPRT Mutagenesis Assays

HPRT mutagenesis was performed as described elsewhere (Hashimoto et al., *Clin. Cancer Res.*, 1:369-376 (1995)). CAPAN1 cells were cultured in RPMI 1640 containing 15% fetal calf serum (medium E) in the presence of ABT-888 and/or 250 nM AZ12594248 for 72 hours, washed, and allowed to recover in drug-free medium for 5 days. Each sample group was trypsinized, replated at 10$^6$ cells/100-mm dish in medium E supplemented with 15 µM 6-TG, cultured until colonies were visible (14-21 days), and analyzed manually for colony formation. At the same time as 6-TG selection, 1000 cells from each sample were plated on triplicate 60-mm dishes in drug-free medium E and allowed to grow into colonies to determine plating efficiency. Mutagenesis frequencies were calculated by dividing the number of colonies on 6-TG-treated plates by the total number of possible colonies (10$^6$ cells×plating efficiency).

Clonogenic Assays

Colony formation assays were performed on siRNA-transfected PEO1 and PEO4 cells 48 hours after the second transfection. Cells were trypsinized and plated at 750 cells/plate in triplicate 60-mm dishes containing medium A, allowed to grow 10-14 days, and stained with Coomassie Brilliant Blue. Colonies containing ≥50 cells were scored manually. To assess methyl methanesulfonate (MMS) sensitivity, PEO1 or PEO4 cells were incubated for 48 hours after the second siRNA treatment, plated onto 60-mm dishes, allowed to adhere for 4 hours, exposed to the indicated concentration of MMS (Sigma-Aldrich) for 1 hour, washed with sterile RPMI 1640, and allowed to grow into colonies in medium A. For drug treatment, cells (without siRNA) were allowed to adhere for 4-6 hours, then treated with the indicated concentrations of ABT-888 and/or AZ12594248 for 72 hours. Following drug treatment, cells were washed with drug-free RPMI 1640, cultured for 10-14 days in medium A, and stained. For HCC1937 and HCC1937/BRCA1 cells, a similar procedure was used with several changes: 1000 cells were plated in medium B, and treatment was continuous for 16-20 days. M059J and M059J+DNA-PKcs were plated at 1000 cells per plate in medium C and treated for 48 hours. GM16666 and 16667 were plated at 1000 cells per plate in medium D and treated for 48 hours.

Immunoblotting

Cells were washed twice with calcium- and magnesium-free Dulbecco's phosphate-buffered saline (PBS) and solubilized in 6 M guanidine hydrochloride containing 250 mM Tris-HCl, pH 8.5 at 20° C., 10 mM EDTA, 1% (v/v) 2-mercaptoethanol, and 1 mM freshly added phenylmethylsulfonyl fluoride. After preparation for electrophoresis as described elsewhere (Kaufmann et al., Blood, 89:2098-2104 (1997)), aliquots containing 50 µg of protein (determined by the bicinchoninic acid method—S10) were separated on SDS-polyacrylamide gels containing 8% (w/v) acrylamide, electrophoretically transferred to nitrocellulose, and probed with immunological reagents as described elsewhere (Kaufmann, Anal. Biochem., 296:283-286 (2001)). 6% polyacrylamide gels were used to resolve DNA-PK; and 4-20% gradient polyacrylamide gels were used to resolve histones.

Immunofluorescence and Confocal Microscopy

Immunofluorescence studies were performed as described elsewhere (Segovis et al., J. Immunol., 182:6933-6942 (2009)) with several modifications. Cells grown on nitric acid-etched coverslips were treated as described, then fixed in 2% (w/v) paraformaldehyde in PBS for 10 minutes at room temperature, washed with PBS, and permeabilized with 0.25% (v/v) Triton X-100 in PBS for 5 minutes. Coverslips were then incubated in blocking buffer consisting of PBS, 1% (v/v) glycerol, 0.1% (w/v) gelatin from cold water fish, 5% (v/v) normal goat serum, 0.1% (w/v) BSA, and 0.4% (w/v) sodium azide for 1 hour at room temperature. Coverslips were incubated overnight at 4° C. in primary antibody (1:500 dilution for phospho-Ser$^{139}$ H2Ax, 1:250 for phospho-Thr$^{2609}$ DNA-PKcs, or 1:250 for phospho-Ser$^{2056}$ DNA-PKcs).

Coverslips were then washed three times with PBS and incubated for 1 h with Alexa Fluor 488- and/or 568-conjugated secondary antibody (Invitrogen) diluted 1:1000. Coverslips were counterstained with 1 µg/mL Hoechst 33258 in PBS, and mounted using UltraLong antifade reagent (Invitrogen). Phospho-H2AX positive cells (defined as having >10 foci/cell) were counted on a Zeiss Axioplan microscope. Confocal images were captured on a Zeiss LSM 710 scanning confocal microscope using a 100×/1.4NA oil-immersion objective. Quantitation and image processing were performed using the Zeiss Zen software package and Adobe Photoshop CS3.

Microhomology Mediated End-Joining Assay (MMEJ)

An assay for MMEJ activity was used as described elsewhere (Fattah et al., PLoS Genet., 6:e1000855 (2010); Verkaik et al., Eur. J. Immunol., 32:701-709 (2002); and Lou et al., J. Biol. Chem., 279:46359-46362 (2004)). Briefly, 2 µg of EcoRV- and AfeI-(NEB) linearized pDVG94 (provided by Z. Lou, Mayo Clinic) was electroporated into cells. Four hours after transfection, PEO1 and PEO4 cells were exposed to varying concentrations of ABT-888 for 72 hours. Following exposure, plasmid DNA was recovered using a Hirt extraction method, phenol-chloroform extracted twice, exposed to 25 U proteinase K (Roche; Indianapolis, Ind.) for 1 hour at 37° C., and ethanol precipitated. Purified DNA was PCR amplified using primers FM30 and DAR5 (Verkaik et al., Eur. J. Immunol., 32:701-709 (2002)). DNA was then digested with BstXI (NEB) for 2 hours at 37° C. Restriction fragments were separated on a 4% sieving MetaPhor agarose gel (Lonza), stained with ethidium bromide, and visualized using a UV light source. As a positive control, M059J cells lacking DNA-PKcs were used. These cells participate in MMEJ, while their paired DNA-PK reconstituted cells do not (Lou et al., J. Biol. Chem., 279:46359-46362 (2004)).

Results

PARP Inhibitor Synthetic Lethality is Independent of XRCC1 and BER

Figure 1:
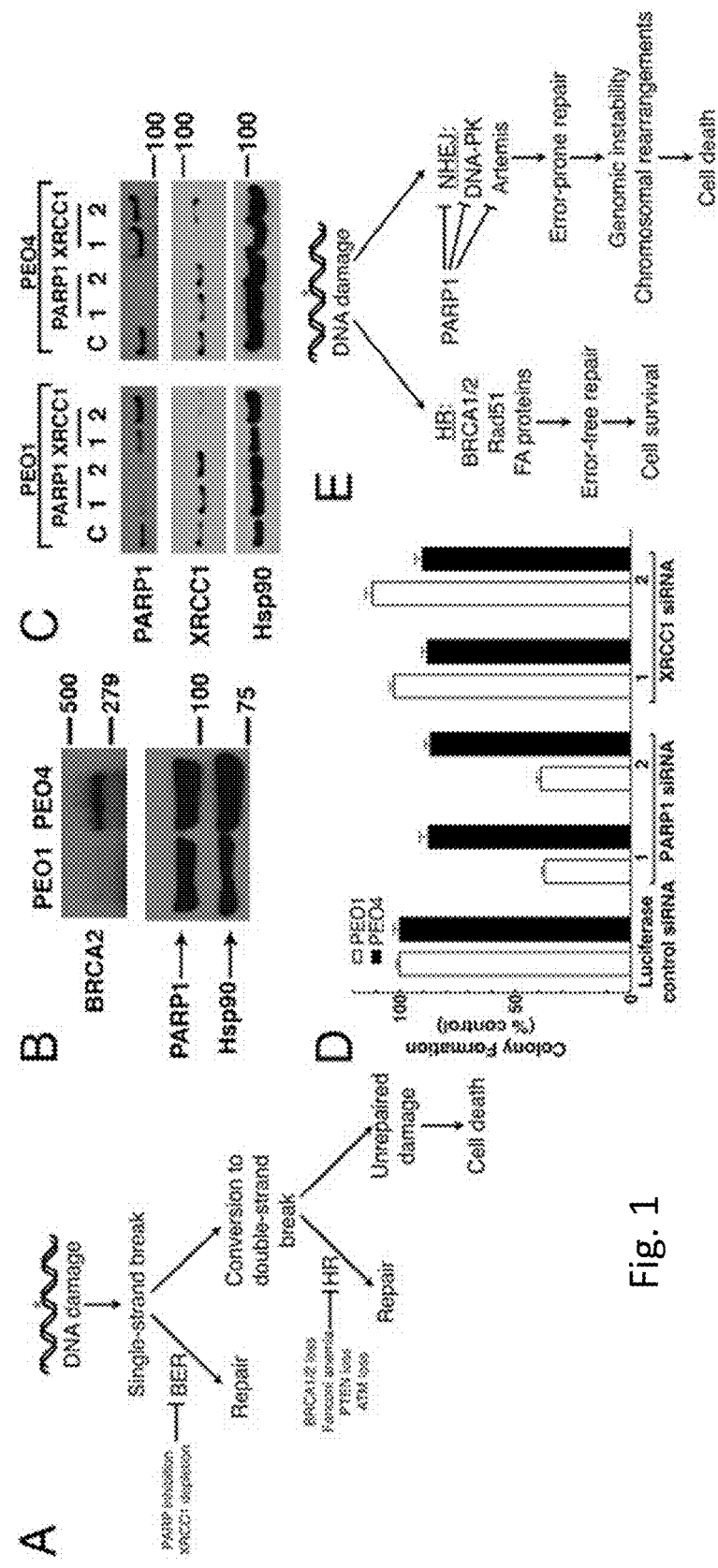
FIG. 1. PARP inhibitor synthetic lethality is independent of XRCC1 and BER. (A) Model explaining previously proposed synthetic lethality of PARP inhibition and HR deficiency. PARP inhibition is thought to induce accumulation of single-strand breaks (SSBs), which are converted to double-strand breaks (DSBs) by collisions with replication machinery. The inability of HR-deficient cells to adequately repair DSBs was thought to result in genomic instability and eventual cell death. (B) Western blotting of cell lysates from PEO1 and PEO4 cells. Blots were probed for BRCA2, PARP1, and Hsp90 (loading control). (C) Western blots demonstrating siRNA-mediated knockdown using luciferase (control), PARP1, or XRCC1 siRNA in PEO1 or PEO4 cells. (D) Clonogenic viability of cells from (C) after siRNA knockdown. Following knockdown, cells were plated onto triplicate plates and allowed to form colonies. All results are reported as means of triplicate plates±SEM, and are representative of 3 independent experiments. (E) An alternate model of PARP inhibitor synthetic lethality centering on error-prone non-homologous end-joining (NHEJ). In this model, PARP1 catalytic activity regulates NHEJ activity, preventing NHEJ components from binding to sites of DNA damage or DNA ends. In the absence of HR and PARP activity, deregulated NHEJ aberrantly processes DNA and introduces chromosomal instability, leading to cell death.

The current model of PARP inhibitor lethality in HR-deficient cells (FIG. 1A) postulates that PARP inhibition induces persistent SSBs through inactivation of BER, and that these breaks are converted to DSBs by collision with replication machinery. This model predicts that disabling BER should recapitulate the effect of PARP inhibition in these cells. To test this model, siRNA-mediated knockdown of XRCC1, an essential protein in BER, was induced (Caldecott, DNA Repair (Amst), 2:955-969 (2003)). These experiments utilized PEO1 and PEO4 cells, a pair of ovarian cancer lines that are derived from the same patient but differ in BRCA2 expression (Sakai et al., Cancer Res., 69:6381-6386 (2009)) (FIG. 1B). PARP1 depletion significantly and reproducibly decreased the clonogenic survival of BRCA2-deficient PEO1 cells, but not BRCA2-expressing PEO4 cells (FIGS. 1C and 1D), confirming previously published results (Bryant et al., Nature, 434:913-917 (2005); and Farmer et al., Nature, 434: 917-921 (2005)). Depletion of XRCC1 did not alter the viability of either cell line (FIGS. 1C and 1D), even though the same XRCC1 knockdown sensitized both lines to the alkylating agent methane methylsulfonate (FIG. 7). Based at least in part on this result and the report that PARP inhibitors fail to increase SSBs in BRCA2-deficient cells (Gottipati et al., Cancer Res., 70:5389-5398 (2010)), the possibility that PARP1 maintained the genomic stability of HR-deficient cells through a mechanism distinct from BER was considered.

PARP Inhibition Induces Phosphorylation of DNA-PK Targets and Enhances NHEJ

In addition to its role in BER, PARP1 has been implicated in the modulation of a variety of nuclear processes, including classical NHEJ (Wang et al., Nucleic Acids Res., 34:6170-6182 (2006); Rouleau et al., Nat. Rev. Cancer, 10:293-301 (2010); and Hochegger et al., EMBO J., 25:1305-1314 (2006)). It was hypothesized that the simultaneous loss of HR and PARP1 might result in deregulation of NHEJ (FIG. 1E). If this model were correct, PARP inhibition in HR-deficient cells would result in increased activation of DNA-PK, increased NHEJ activity, and increased genomic instability resulting from this error-prone pathway. Importantly, this alternative model suggests that inhibition of NHEJ using genetic or pharmacological approaches should diminish the effects of PARP inhibitors on all of these processes.

To test these, PEO1 cells were incubated with the PARP inhibitor ABT-888 (Penning et al., J. Med. Chem., 52:514-523 (2008)) (FIG. 2A), and the phosphorylation of DNA-PK substrates were examined. The epitopes examined included the phosphorylation site of DNA-PKcs at Thr$^{2609}$, which must be phosphorylated for efficient NHEJ (Chan et al., Genes Dev., 16:2333-2338 (2002), and Ser$^{139}$ of H2AX, which undergoes DNA damage-induced phosphorylation by several kinases, including activated DNA-PKcs (Stiff et al., Cancer Res., 64:2390-2396 (2004)). Both of these sites were phosphorylated in a dose-dependent manner as poly(ADP-ribosyl)ation decreased in ABT-888-treated PEO1 cells (FIG. 2A). Addition of the DNA-PK inhibitor AZ 12594248 (Hingorani et al., Cancer Res., 68:9771-9778 (2008)) prevented the ABT-888-induced phosphorylation of DNA-PKcs and H2AX, whereas the ATM inhibitor KU55933 (Hickson et al., Cancer Res., 64:9152-9159 (2004)) did not (FIG. 2B). Likewise, DNA-PKcs autophosphorylation at Ser$^{2056}$ (Uematsu et al., J. Cell. Biol., 177:219-229 (2007)) increased when PEO1 cells were treated with ABT-888 (FIG. 8A), and this phosphorylation was reversed by DNA-PK inhibition (FIGS. 8B and 8C).

Additional experiments in PEO1 cells demonstrated that ABT-888 induced phospho-H2AX foci, which was capable of being diminished by inhibiting DNA-PK (FIGS. 2C and 2D). These phospho-H2AX foci colocalized with phosphorylated DNA-PKcs after PARP inhibition (FIG. 2D, third row). Moreover, formation of foci and phosphorylation of DNA-PKcs were both reduced by the addition of a DNA-PK inhibitor (FIG. 2D, fourth row). Similarly, downregulation of Ku80 or Artemis, a nuclease responsible for processing DNA ends in NHEJ (Ma et al., *Cell*, 108:781-794 (2002) and Drouet et al., *J. Biol. Chem.*, 281:27784-27793 (2006)), reduced ABT-888 induced phospho-H2AX foci in PEO1 cells (FIG. 9). In contrast, PARP inhibition failed to induce phosphorylation of both DNA-PKcs and H2AX in PEO4 cells (FIG. 8D). Thus, PARP inhibitors induced DNA-PK activation, as manifested by phosphorylation of DNA-PK substrates and formation of foci containing phosphorylated DNA-PKcs, only in BRCA2-deficient PEO1 and not BRCA2-positive PEO4 cells.

Figure 3:
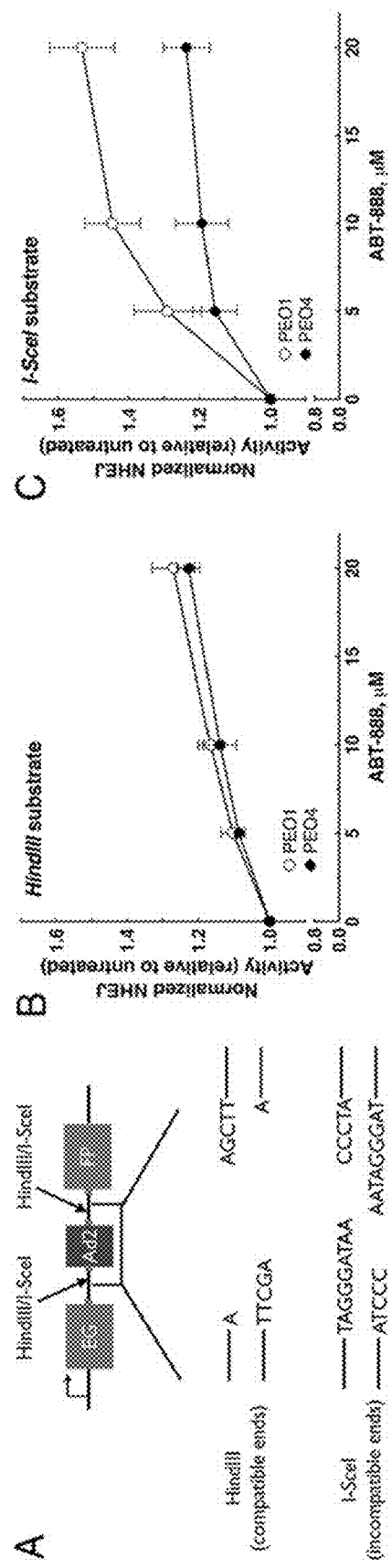
FIG. 3. Error-prone NHEJ activity is enhanced by PARP inhibitors in PEO1 cells. (A) Schematic of the in vivo NHEJ assay. Pem1-Ad2-EGFP is an EGFP-containing vector with a 2.4 kb intron (Pem1) and one exon (Ad2) inserted into the EGFP cassette. Pem1-Ad2-EGFP was cut with either HindIII or I-SceI to produce linearized substrate with compatible overhangs or incompatible inverted overhangs, respectively.

To directly measure the effect of PARP inhibition on NHEJ activity in vivo, a validated reporter assay was used (Wang et al., *Nucleic Acids Res.*, 34:6170-6182 (2006); Seluanov et al., *Proc. Natl. Acad. Sci. USA*, 101:7624-7629 (2004) and Fattah et al., *PLoS Genet.*, 6:e1000855 (2010)) (FIG. 3A). After transfection with linearized Pem1-EGFP-Ad2, PEO1 and PEO4 cells were incubated with diluent or ABT-888. Successful end-joining recircularizes the plasmid, restoring EGFP expression that can be detected by flow cytometry. Substrate linearization with HindIII produces cohesive 4-bp overhangs, while digestion with I-SceI produces an inverted overhang that requires nucleolytic end-processing prior to successful recircularization. Using this assay, a small increase in end-joining was detected after ABT-888 treatment in both PEO1 and PEO4 cells transfected with HindIII-linearized plasmid (FIG. 3B). Strikingly, ABT-888 induced a pronounced increase in end-joining of the I-SceI-linearized substrate in PEO1 cells compared to PEO4 cells (FIGS. 3C and 10). Because the I-SceI substrate had ends that require nucleolytic processing prior to end-joining, the disproportionate increase in recircularization of this substrate, but not the HindIII substrate, implied that PARP inhibition increases error-prone repair selectively in BRCA2-deficient PEO1 cells.

An alternate form of end-joining, microhomology-mediated end joining (MMEJ) has been described in the absence of DNA-PKcs (Wang et al., *Nucleic Acids Res.*, 31:5377-5388 (2003)). Using an assay for MMEJ (Fattah et al., *PLoS Genet.*, 6:e1000855 (2010) and Verkaik et al., *Eur. J. Immunol.*, 32:701-709 (2002)) (FIG. 11A) that readily detected MMEJ in DNA-PKcs deficient M059J cells (FIG. 11B, lanes 11 and 12), induction of MMEJ in PEO1 or PEO4 cells exposed to ABT-888 was not detected (FIGS. 11B and 11C), ruling out the induction of MMEJ by PARP inhibition. These results collectively demonstrate that PARP inhibition selectively enhances DNA-PK activity and error-prone NHEJ activity in PEO1 but not PEO4 cells.

PARP Inhibitor-Induced Genomic Instability is Driven by NHEJ

In BRCA-deficient cells, PARP inhibitors induce chromosomal instability typified by the accumulation of chromosomal breaks and radial structures. Consistent with these reports, ABT-888 induced the formation of chromosome breaks and aberrant radial structures in PEO1 cells (FIGS. 4A and 4B), but not in PEO4 cells (FIG. 4B). Importantly, addition of the DNA-PK inhibitor substantially diminished this effect, indicating that NHEJ plays a role in the development of aberrant chromosomal structures following PARP inhibition in PEO1 cells.

To extend these studies to the single-gene level, forward mutagenesis assays were performed to measure the mutation rate of the hypoxanthine-guanine phosphoribosyl transferase (HPRT) locus in BRCA2-mutant cells exposed to a PARP inhibitor. The toxicity of 6-thioguanine (6-TG) is dependent on the expression of active HPRT; as a consequence, only cells with mutations at the X-linked HPRT locus are able to survive in 6-TG supplemented medium. To perform these experiments, CAPAN1 cells, a BRCA2-mutant cell line derived from a male pancreatic cancer patient, were used to ensure that the model system had only one copy of the HPRT gene. CAPAN1 cells treated with PARP inhibitor formed more colonies in the presence of 6-TG, indicating increased mutation frequency compared to diluent controls (FIG. 4C). As was the case with chromosomal aberrations, co-administration of the DNA-PK inhibitor markedly reduced the mutation frequency. Overall, these experiments demonstrate that NHEJ increases genomic damage, both at the chromosomal level and the individual gene level, when PARP is inhibited.

Disabling NHEJ Diminishes PARP Inhibitor Hypersensitivity in BRCA2-Deficient Cells To determine whether the previous results extend to cell survival, clonogenic assays were performed using paired cell lines treated with ABT-888 after various alterations in the NHEJ pathway. Knockdown of Ku80, an essential component of NHEJ (Weterings and Chen, *Cell Res.*, 18:114-124 (2008), had little effect by itself but markedly enhanced the survival of BRCA2-deficient PEO 1 cells treated with ABT-888 (FIGS. 5A and 5B). In contrast, BRCA2-positive PEO4 cells were resistant to the effects of ABT-888; and this was unaffected by Ku80 siRNA (FIGS. 5A and 5B). To ensure that the sensitivity of PEO1 cells was not an off-target effect of ABT-888, the same experiment was performed by knocking down PARP1 and/or Ku80 using siRNA (FIGS. 5C and 5D). Like ABT-888, PARP1 depletion decreased the clonogenic survival of PEO1 cells, but not PEO4 cells; and Ku80 knockdown reversed the effect of the PARP1 siRNA. Similar to Ku80 knockdown, siRNA depletion of Artemis also reversed the lethality of ABT-888 in PEO1 cells (FIG. 5E). Likewise, co-administration of the DNA-PK inhibitor AZ 12594248 diminished the effects of ABT-888 (FIGS. 5F, 13A, and 13B) and another PARP inhibitor, AZD2281 (FIG. 13C). Similar results were observed in BRCA2-mutant CAPAN1 cells, where DNA-PK inhibition again mitigated the toxicity of PARP inhibition (FIG. 14). In short, inhibition or downregulation of multiple components of the NHEJ pathway diminished the toxicity of PARP 1 inhibition in BRCA2-deficient cells, indicating that the toxicity of PARP 1 inhibition is dependent on NHEJ in this context.

NHEJ is Also Responsible for PARP Inhibitor Lethality in Other HR-Deficient Contexts In addition to BRCA2, previous studies documented synthetic lethality between PARP inhibition and loss of other HR components, such as BRCA1 (Farmer et al., *Nature*, 434:917-921 (2005)) and ATM (Williamson et al., *Mol. Canc. Ther.*, 9:347-357 (2010) and Weston et al., *Blood*, 116:4578-4587 (2010)). In HCC1937 cells, which lack BRCA1 (Tomlinson et al., *Cancer Res.*, 58:3237-3242 (1998)) (FIG. 6A, inset), addition of the DNA-PK inhibitor diminished ABT-888 sensitivity (FIG. 6A) just as it did in PEO1 cells. Moreover, in HCC1937 cells, inhibition of DNA-PK also diminished formation of H2AX foci (FIG. 15A) and inhibited ABT-888 induced colocalization of phospho-Thr$^{2609}$-DNA-PK and phospho-Ser$^{139}$-H2AX in foci (FIG. 15B). Likewise, BRCA1 knockdown sensitized DNA-PKcs-reconstituted M059J cells to ABT-888 (FIGS. 6B and 6C). Importantly, parental M059J cells lacking DNA-PKcs were not sensitized by BRCA1 knockdown (FIGS. 6B and 6C), providing independent genetic evidence for the important role of DNA-PKcs in the synthetic lethality of HR deficiency and PARP inhibition.

To extend these results to ATM deficiency, GM16666 and GM16667 cells, an ATM-deficient line and its ATM-reconstituted counterpart (Ziv et al., *Oncogene*, 15:159-167 (1997)), were examined (FIG. 6D, inset). Similar to BRCA1- and BRCA2-deficient cells, GM16666 cells exhibited heightened sensitivity to ABT-888; and inhibition of DNA-PK reversed this effect (FIG. 6D). Collectively, the results presented in FIG. 6 not only demonstrate that the effect of DNA-PK inhibition on cellular sensitivity to PARP inhibition extends to other HR-deficient backgrounds, but also provide genetic evidence that NHEJ plays a vital role in hypersensitivity of HR-deficient cells to PARP inhibitors.

Taken together, these results demonstrate that PARP inhibitor treatment induces phosphorylation of DNA-dependent protein kinase (DNA-PK) substrates and stimulates error-prone nonhomologous end-joining (NHEJ) selectively in HR-deficient cells. Notably, inhibiting DNA-PK activity reverses the genomic instability previously reported in these cells after PARP inhibition. Importantly, when NHEJ is disabled because of loss of one of the components (e.g., loss of DNA-PKcs expression in M059J cells), silencing of one of the components (e.g., siRNA that diminishes expression of artemis or Ku80) or treatment with a pharmacological inhibitor (e.g., AZ12594248, which inhibits DNA-PKcs), the lethality of PARP inhibition or downregulation in cell lines lacking BRCA2, BRCA1, or ATM is rescued. Collectively, these results not only implicate PARP1 catalytic activity in the regulation of NHEJ in HR-deficient cells, but also indicate that deregulated NHEJ plays a major role in generating the genomic instability and cytotoxicity in HR-deficient cells treated with PARP inhibitors.

Example 2

Artemis

In a NHEJ substrate assay, a linearized Pem1-Ad2-EGFP was transfected into PEO 1 and PEO4 cells, a pair of ovarian cancer cell lines that were derived from the same patient but differ in BRCA2 expression, that were exposed to a PARP inhibitor (ABT-888/veliparib) (FIG. 16A). ABT-888 had little effect on the re-circularization of a substrate with compatible ends (HindIII-linearized), but re-circularization of a substrate that required end-resection (I-SceI-linearized) was significantly increased in PEO1 cells compared to PEO4 cells (FIG. 16B; p=0.0136 unpaired t-test). The following was performed to determine whether Artemis polypeptide, a nucleolytic enzyme involved in NHEJ (Drouet et al., *J. Biol. Chem.*, 281:27784-27793 (2006) and Ma et al., *Cell*, 108: 781-794 (2002)), was responsible for end-resection in these cells. PEO1 cells transfected with two siRNAs directed to Artemis displayed a significant reduction in the re-circularization that was limited to the I-SceI linearized substrate (FIG. 16C; p=0.0021 and 0.0301, one sample t-test).

To determine if the Artemis polypeptide was essential for the DNA damage signaling induced by PARP inhibitor exposure in BRCA2-deficient cells, Artemis expression was stably knocked down in PEO1 cells using two shRNA constructs targeted to different portions of the Artemis mRNA (FIG. 16D). Knockdown of Artemis expression resulted in reduced phosphorylation of H2AX and RPA, two markers of DNA damage-induced signaling, as assayed by Western blotting (FIG. 16E) and confocal microscopy (FIG. 16F). Collectively, these results demonstrate that the Artemis polypeptide was necessary for the signaling of DNA damage within a BRCA2-deficient background. In addition, Artemis was located at the sites of DNA damage after treatment with ABT-888 (FIG. 17).

The following was performed to determine if an Artemis knockdown altered the sensitivity of PEO1 cells to PARP inhibitors and cisplatin. Artemis knockdown conferred resistance to ABT-888 and cisplatin (FIGS. 18A and 18B). As a control, the effect of Artemis knockdown on sensitivity to ionizing radiation was assessed. This experiment demonstrated that Artemis knockdown sensitized cells to ionizing radiation (FIG. 18C). To ensure that these results were not unique to PEO1 cells, the same experiments were performed in a different BRCA2-mutant cell line, CAPAN1 cells, with similar results (FIGS. 18D-F). These results demonstrate that diminished NHEJ—and particularly diminished Artemis—conveys resistance to PARP inhibitors and cisplatin.

To address the potential clinical importance of Artemis in regulating sensitivity to cisplatin and PARP inhibitors, The Cancer Genome Atlas (TCGA) database (The Cancer Genome Atlas Research Network, *Nature*, 474:609-615 (2011)), a publically available database containing information about gene expression, was interrogated to identify NHEJ components that correlate with prolonged tumor regression in BRCA-mutant ovarian cancer patients. This analysis was confined to patients with sequence-verified BRCA1 or BRCA2 mutations, one of the major subsets of ovarian cancer patients for whom PARP inhibitors are currently being developed. The patients whose data are available in this database were treated with platinum-based (but unspecified) therapy, not with PARP inhibitors. In comparing the gene expression of tumor material from patients who maintained remission to those who had recurrences, it was found that disease-free individuals had a significantly higher expression of Artemis (DCLREJC; p=0.0026, unpaired t-test; FIG. 20). In contrast, no significant difference in expression for DNA-PKcs (PRKDC), Ku80 (XRCC 5), Ku70 (XRCC6), XRCC4 (XRCC4), Cernunnos/XLF (NHEJ1), DNA Ligase IV (LIGIV), 53BP1 (TP53BP1), or PARP1 (PARP1) was observed between these two groups. The following was performed to determine whether Artemis expression correlated with prolonged progression-free survival as well. BRCA-mutation carriers with high expression of Artemis (upper quartile of expression) were compared to the remainder of the patient cohort. Patients with high expression of Artemis had a significant delay in disease progression (p=0.0331, Gehan's generalized Wilcoxon test; FIG. 21). Collectively, biostatistical analysis of gene expression in BRCA-mutant ovarian tissue suggests that Artemis expression correlates with progression-free survival.

The results provided herein demonstrate that NHEJ and specifically, the nuclease Artemis, is a modulator of response and survival in BRCA1/2 mutation carriers whose cancer (e.g., ovarian cancer) is treated with either PARP inhibitors or platinating agents.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating cancer, wherein said method comprises:
   (a) detecting the absence of a reduced level of functionality of a non-homologous end-joining pathway in homologous recombination-deficient cancer cells from a mammal having cancer, and
   (b) administering, to said mammal, a PARP inhibitor or platinating agent under conditions wherein the number of viable cancer cells within said mammal is reduced.

2. The method of claim 1, wherein said cancer cells are ovarian or breast cancer cells.

3. The method of claim 1, wherein said mammal is a human.

4. The method of claim 1, wherein said detecting step comprises detecting the absence of a reduced level expression of an artemis mRNA or polypeptide.

5. The method of claim 1, wherein said method comprises administering said PARP inhibitor to said mammal.

6. The method of claim 5, wherein said PARP inhibitor is Iniparib, Olaparib, Veliparib, or Rucaparib.

7. The method of claim 1, wherein said method comprises administering said platinating agent to said mammal.

8. The method of claim 7, wherein said platinating agent is cisplatin, carboplatin, or oxaliplatin.

9. The method of claim 1, wherein said homologous recombination-deficient cancer cells are BRCA1-deficient cancer cells.

10. The method of claim 1, wherein said homologous recombination-deficient cancer cells are BRCA2-deficient cancer cells.

11. The method of claim 1, wherein said homologous recombination-deficient cancer cells are ATM-deficient cancer cells.

12. A method for treating cancer, wherein said method comprises:
   (a) detecting the presence of a reduced level of functionality of a non-homologous end-joining pathway in homologous recombination-deficient cancer cells from a mammal having cancer, and
   (b) administering, to said mammal, a cancer treatment agent other than a PARP inhibitor or platinating agent under conditions wherein the number of viable cancer cells within said mammal is reduced.

13. The method of claim 12, wherein said cancer cells are ovarian or breast cancer cells.

14. The method of claim 12, wherein said mammal is a human.

15. The method of claim 12, wherein said detecting step comprises detecting the presence of a reduced level expression of an artemis mRNA or polypeptide.

16. The method of claim 12, wherein said method comprises administering paclitaxel, topotecan, temozolmide, or gemcitabine to said mammal.

17. The method of claim 12, wherein said homologous recombination-deficient cancer cells are BRCA1-deficient cancer cells.

18. The method of claim 12, wherein said homologous recombination-deficient cancer cells are BRCA2-deficient cancer cells.

19. The method of claim 12, wherein said homologous recombination-deficient cancer cells are ATM-deficient cancer cells.

* * * * *

SEQUENCE LISTING

<160> NUMBER OF SEQ ID NOS: 13

<210> SEQ ID NO 1
<211> LENGTH: 21
<212> TYPE: RNA
<213> ORGANISM: Homo sapiens

<400> SEQUENCE: 1
cugaagagag cuagaacaga a                                              21

<210> SEQ ID NO 2
<211> LENGTH: 21
<212> TYPE: RNA
<213> ORGANISM: Homo sapiens

<400> SEQUENCE: 2
uuaggagucc agguucauga a                                              21

<210> SEQ ID NO 3
<211> LENGTH: 20
<212> TYPE: RNA
<213> ORGANISM: Homo sapiens

<400> SEQUENCE: 3
gcgaguaacc agcucauaau                                                20

<210> SEQ ID NO 4
<211> LENGTH: 21
<212> TYPE: RNA
<213> ORGANISM: Homo sapiens

<400> SEQUENCE: 4
aagagcuaau ccucaagucu u                                              21

<210> SEQ ID NO 5
<211> LENGTH: 21
<212> TYPE: RNA
<213> ORGANISM: Homo sapiens

<400> SEQUENCE: 5
cuuacgcuga guacuucgau u                                              21

<210> SEQ ID NO 6
<211> LENGTH: 21
<212> TYPE: RNA
<213> ORGANISM: Homo sapiens

<400> SEQUENCE: 6
aagccuccgc uccugaacaa u                                              21

<210> SEQ ID NO 7
<211> LENGTH: 21
<212> TYPE: RNA
<213> ORGANISM: Homo sapiens

<400> SEQUENCE: 7
aagauagagc gugaaggcga a                                              21

<210> SEQ ID NO 8
<211> LENGTH: 21
<212> TYPE: RNA
<213> ORGANISM: Homo sapiens

-continued

```
<400> SEQUENCE: 8
agggaagagg aaguuggauu u                                      21

<210> SEQ ID NO 9
<211> LENGTH: 21
<212> TYPE: RNA
<213> ORGANISM: Homo sapiens

<400> SEQUENCE: 9
cucgacucac ugugcagaau u                                      21

<210> SEQ ID NO 10
<211> LENGTH: 58
<212> TYPE: DNA
<213> ORGANISM: Homo sapiens

<400> SEQUENCE: 10
ccggcccacc taattgtact gaattctcga gaattcagta caattaggtg ggtttttg    58

<210> SEQ ID NO 11
<211> LENGTH: 58
<212> TYPE: DNA
<213> ORGANISM: Homo sapiens

<400> SEQUENCE: 11
ccggccctaa gtttacttct ctaaactcga gtttagagaa gtaaacttag ggtttttg    58

<210> SEQ ID NO 12
<211> LENGTH: 36
<212> TYPE: DNA
<213> ORGANISM: Artificial Sequence
<220> FEATURE:
<223> OTHER INFORMATION: assay products

<400> SEQUENCE: 12
ccaatcagca tcagctgggg ttagtcgtag tcgacc                      36

<210> SEQ ID NO 13
<211> LENGTH: 24
<212> TYPE: DNA
<213> ORGANISM: Artificial Sequence
<220> FEATURE:
<223> OTHER INFORMATION: assay products

<400> SEQUENCE: 13
ccaatcagct ggggttagtc gacc                                   24
```